United States Patent
Etou et al.

(10) Patent No.: US 11,655,199 B2
(45) Date of Patent: May 23, 2023

(54) METHODS FOR PRODUCING HALOGENATED ALKENE COMPOUND AND FLUORINATED ALKYNE COMPOUND

(71) Applicant: DAIKIN INDUSTRIES, LTD., Osaka (JP)

(72) Inventors: Yuusuke Etou, Osaka (JP); Shingo Nakamura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/407,730

(22) Filed: Aug. 20, 2021

(65) Prior Publication Data

US 2021/0380506 A1  Dec. 9, 2021

Related U.S. Application Data

(63) Continuation of application No. PCT/JP2020/006018, filed on Feb. 17, 2020.

(30) Foreign Application Priority Data

| Feb. 21, 2019 | (JP) | JP2019-029426 |
| Jul. 3, 2019 | (JP) | JP2019-124533 |
| Nov. 22, 2019 | (JP) | JP2019-211183 |

(51) Int. Cl.
| C07C 17/25 | (2006.01) |
| C07C 21/18 | (2006.01) |
| C07C 21/22 | (2006.01) |
| C07C 17/087 | (2006.01) |

(52) U.S. Cl.
CPC ............ *C07C 17/087* (2013.01); *C07C 17/25* (2013.01); *C07C 21/18* (2013.01); *C07C 21/22* (2013.01)

(58) Field of Classification Search
CPC .................................................... C07C 17/25
See application file for complete search history.

(56) References Cited

U.S. PATENT DOCUMENTS

| 6,031,141 | A | * | 2/2000 | Mallikarjuna | .......... | C07C 17/25 |
| | | | | | | 570/171 |
| 2006/0106263 | A1 | | 5/2006 | Miller et al. | | |
| 2008/0051611 | A1 | * | 2/2008 | Wang | .................... | C07C 17/087 |
| | | | | | | 570/166 |

FOREIGN PATENT DOCUMENTS

| CN | 101265155 | 9/2008 |
| JP | 2004-292329 | 10/2004 |
| JP | 2007-320874 | 12/2007 |
| JP | 2009-269891 | 11/2009 |
| JP | 2010-189338 | 9/2010 |
| JP | 2015-530417 | 10/2015 |
| JP | 2017-515789 | 6/2017 |
| WO | 2012/067864 | 5/2012 |
| WO | 2014/052695 | 4/2014 |
| WO | 2015/120250 | 8/2015 |

OTHER PUBLICATIONS

Machine translation of Patent No. JP2010189338A, Sep. 2, 2010, pp. 1-11 (Year: 2010).*
International Search Report dated Apr. 28, 2020 in International (PCT) Application No. PCT/JP2020/006018.
Chambers et al., "Eliminations from 2H-Heptafluorobut-2-ene", Journal of Fluorine Chemistry, 1996, vol. 79, pp. 121-124.
Extended European Search Report dated Nov. 14, 2022 in corresponding European Patent Application No. 20759907.7.

* cited by examiner

*Primary Examiner* — Medhanit W Bahta
(74) *Attorney, Agent, or Firm* — Wenderoth, Lind & Ponack, L.L.P.

(57) ABSTRACT

A halogenated alkene compound and a fluorinated alkyne compound are obtained at a high conversion rate and high selectivity by employing any of the following methods (1) to (4):

(1) a halogenated butane compound represented by $CX^1X^2X^3CHX^4CFHCX^5X^6X^7$, wherein $X^1$, $X^2$, $X^3$, $X^4$, $X^5$, $X^6$, and $X^7$ are the same or different and each is a halogen atom, to a dehydrofluorination reaction;

(2) a halogenated butene compound represented by $CX^1X^2X^3CX^4{=}CHCX^5X^6X^7$, wherein $X^1$, $X^2$, $X^3$, $X^4$, $X^5$, $X^6$, and $X^7$ are as defined above, to a dehydrohalogenation reaction;

(3) a halogenated alkane compound represented by $CHX^8A^1CHX^9A^2$, wherein $A^1$ and $A^2$ are each a fluorine atom or a perfluoroalkyl group, and $X^8$ and $X^9$ are the same or different and each is a halogen atom, to a dehydrohalogenation reaction in the presence of a catalyst in a gas phase; and (4) a halogenated alkene compound represented by $CX^8A^1{=}CHA^2$, wherein $A^1$, $A^2$, and $X^8$ are as defined above, to a dehydrohalogenation reaction in the presence of a catalyst.

8 Claims, 2 Drawing Sheets

METHODS FOR PRODUCING HALOGENATED ALKENE COMPOUND AND FLUORINATED ALKYNE COMPOUND

TECHNICAL FIELD

The present disclosure relates to methods for producing a halogenated alkene compound and a fluorinated alkyne compound.

BACKGROUND ART

As a method for producing a halogenated alkene compound, for example, in PTL 1, a starting material such as $CF_3CHClCHClCCl_3$, $CF_3CCl_2CH_2CCl_3$, $CF_3CClHCHFCCl_3$, or $CF_3CClFCH_2CCl_3$ is reacted with hydrogen fluoride in the presence of a chromium oxyfluoride catalyst, and dehydrofluorination is carried out while fluorination, thereby obtaining $CF_3CF=CHCF_3$.

CITATION LIST

Patent Literature

PTL 1: WO2012/067864

SUMMARY

The present disclosure includes the following configurations.

Item 1. A method for producing a halogenated butene compound represented by formula (2A):

$$CX^1X^2X^3CX^4=CHCX^5X^6X^7 \quad (2A)$$

wherein $X^1$, $X^2$, $X^3$, $X^4$, $X^5$, $X^6$, and $X^7$ are the same or different and each is a halogen atom,
the method comprising subjecting a halogenated butane compound represented by formula (1A):

$$CX^1X^2X^3CHX^4CFHCX^5X^6X^7 \quad (1A)$$

wherein $X^1$, $X^2$, $X^3$, $X^4$, $X^5$, $X^6$, and $X^7$ are as defined above, to a dehydrofluorination reaction.

Advantageous Effects of Invention

According to the present disclosure, a halogenated alkene compound and a fluorinated alkyne compound can be synthesized at a high conversion rate and high selectivity.

BRIEF DESCRIPTION OF DRAWINGS

In FIG. 1, the generated hydrogen fluoride can be separated in a rectification column.

In FIG. 2, the generated hydrogen halide can be removed using a hydrogen halide removal agent (removal column).

DESCRIPTION OF EMBODIMENTS

Figure 1:
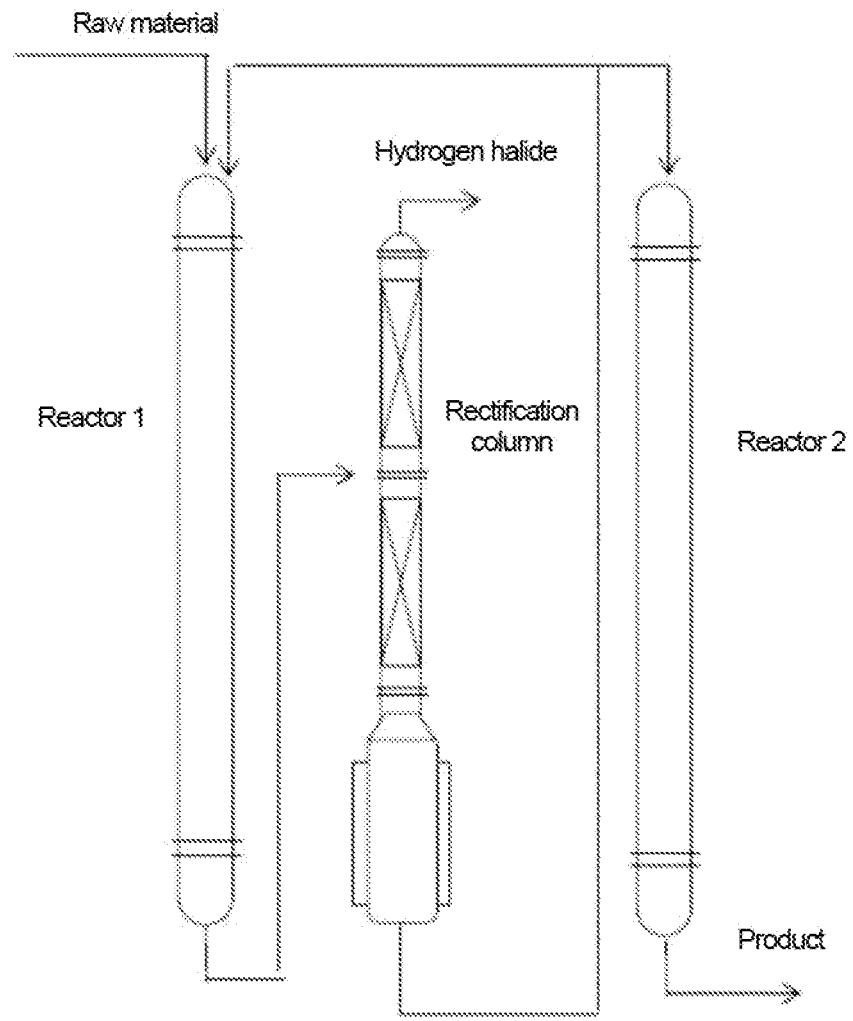
FIG. 1 is a view schematically showing a method for producing an alkene (halogenated butene compound or halogenated alkene compound) and an alkyne (halogenated butyne compound or fluorinated alkyne compound) in the present disclosure.

In the present specification, the term "comprise" is a concept including "comprising," "consisting essentially of," and "consisting of." In the present specification, the numerical range indicated by "A to B" means A or more and B or less.

In the present disclosure, "selectivity" means the ratio (mol %) of the total molar amount of the target compound contained in the effluent gas from the reactor outlet, based on the total molar amount of compounds other than the raw material compound in the effluent gas.

In the present disclosure, "conversion rate" means the ratio (mol %) of the total molar amount of compounds other than the raw material compound contained in the effluent gas from the reactor outlet, based on the molar amount of the raw material compound supplied to the reactor.

Conventionally, in PTL 1, a starting material such as $CF_3CHClCHClCCl_3$, $CF_3CCl_2CH_2CCl_3$, $CF_3CClHCHFCCl_3$, or $CF_3CClFCH_2CCl_3$ was reacted with hydrogen fluoride in the presence of a chromium oxyfluoride catalyst, and dehydrofluorination was carried out while fluorination, thereby obtaining $CF_3CF=CHCF_3$. However, the yield thereof was merely 14.8%.

From the above, the yield was merely 14.8% according to the conventional method. According to the production method of the present disclosure, a halogenated alkene compound and a fluorinated alkyne compound can be synthesized at a higher conversion rate and higher selectivity in comparison to the conventional method.

1. Methods for Producing Halogenated Butene Compound and Halogenated Butyne Compound 1-1: Method for Producing Halogenated Butene Compound from Halogenated Butane Compound The method for producing a halogenated butene compound of the present disclosure is a method for producing a halogenated butene compound represented by formula (2A):

$$CX^1X^2X^3CX^4=CHCX^5X^6X^7 \quad (2A)$$

wherein $X^1$, $X^2$, $X^3$, $X^4$, $X^5$, $X^6$, and $X^7$ are the same or different and each is a halogen atom,
the method comprising subjecting a halogenated butane compound represented by formula (1A):

$$CX^1X^2X^3CHX^4CFHCX^5X^6X^7 \quad (1A)$$

wherein $X^1$, $X^2$, $X^3$, $X^4$, $X^5$, $X^6$, and $X^7$ are as defined above, to a dehydrofluorination reaction.

According to the present disclosure, when the halogenated butane compound represented by formula (1A) is subjected to a dehydrofluorination reaction, a halogenated butene compound represented by formula (2A) in which 1 mol of hydrogen fluoride is eliminated per mol of the halogenated butane compound represented by formula (1A) can be selectively obtained. In addition, the elimination reaction of hydrogen halide represented by $HX^4$ from the halogenated butene compound represented by formula (2A) is unlikely to occur continuously. Further, according to the present disclosure, as the halogenated butene compound represented by formula (2A), the E-isomer can be selectively synthesized among the geometric isomers. The reason for this is as follows. Since the α-carbon of trihalogenated methyl groups, such as a $CF_3$ group, becomes electron-deficient due to the electron attraction effect of the trihalogenated methyl groups, such as a $CF_3$ group, halogenated anions, such as fluorine anions, are less likely to desorb. As a result, halogenated butene is produced, instead of halogenated butyne. Further, selective synthesis of the E-isomer is because the trans configuration is more energetically stable due to steric hindrance of the trihalogenated methyl groups, such as a $CF_3$ group.

(1-1-1) Raw Material Compound (Halogenated Butane Compound)

The halogenated butane compound as a substrate that can be used in the production method of the present disclosure is, as described above, a halogenated butane compound represented by formula (1A):

$$CX^1X^2X^3CHX^4CFHCX^5X^6X^7 \quad (1A)$$

wherein $X^1$, $X^2$, $X^3$, $X^4$, $X^5$, $X^6$, and $X^7$ are the same or different and each is a halogen atom.

In formula (1A), examples of the halogen atom represented by $X^1$, $X^2$, $X^3$, $X^4$, $X^5$, $X^6$, and $X^7$ include a fluorine atom, a chlorine atom, a bromine atom, and an iodine atom.

In the halogenated butane compound, which is a substrate, all of $X^1$, $X^2$, $X^3$, $X^4$, $X^5$, $X^6$, and $X^7$ are preferably fluorine atoms or chlorine atoms, and more preferably fluorine atoms, from the viewpoint that a halogenated butene compound can be produced particularly at a high conversion rate, yield, and selectivity.

$X^1$, $X^2$, $X^3$, $X^4$, $X^5$, $X^6$, and $X^7$ may be the same or different.

Specific examples of the halogenated butane compound as a substrate that satisfies the above conditions include $CF_3CFHCFHCF_3$, $CCl_3CClHCFHCCl_3$, $CBr_3CBrHCFHCBr_3$, and the like. These halogenated butane compounds can be used singly or in combination of two or more. Such halogenated butane compounds can be known or commercially available products.

(1-1-2) Dehydrofluorination Reaction

In the step of subjecting the halogenated butane compound to a dehydrofluorination reaction in the present disclosure, for example, in the halogenated butane compound represented by formula (1A) as a substrate, $X^1$, $X^2$, $X^3$, $X^4$, $X^5$, $X^6$, and $X^7$ are more preferably fluorine atoms.

That is, this reaction is preferably a dehydrofluorination reaction according to the following reaction formula:

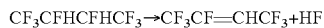

$$CF_3CFHCFHCF_3 \rightarrow CF_3CF=CHCF_3 + HF$$

The step of subjecting the halogenated butane compound to a dehydrofluorination reaction in the present disclosure can be performed in the liquid phase or gas phase. Particularly from the viewpoint of productivity, it is preferable to perform the step in the gas phase.

The step of subjecting the halogenated butane compound to a dehydrofluorination reaction in the present disclosure is preferably performed in the presence of a catalyst and/or a base, from the viewpoint that the target compound can be obtained at a higher selectivity and higher conversion rate. More specifically, when a liquid-phase reaction is employed, the step is preferably performed in the presence of a base and optionally a catalyst, and when a gas-phase reaction is employed, the step is preferably performed in the presence of a catalyst. The details of the catalyst and base in each case are described later.

(1-1-2-1) Liquid-Phase Reaction

When the step of subjecting the halogenated butane compound to a dehydrofluorination reaction in the present disclosure is performed in the liquid phase, the yield of the target compound can be further improved, for example, by using a metal container, and increasing the liquid component by applying pressure and raising the boiling point of the raw material.

When the step of subjecting the halogenated butane compound to a dehydrofluorination reaction in the present disclosure is performed in the liquid phase, it is preferable to first prepare a solution of the halogenated butane compound represented by formula (1A), and then proceed with the reaction in the presence of a base.

Solvent

As the solvent in the halogenated butane compound solution, both aqueous and non-aqueous solvents can be used. Preferred examples of non-aqueous solvents include carbonate esters, such as dimethyl carbonate, ethyl methyl carbonate, diethyl carbonate, methyl propyl carbonate, and ethyl propyl carbonate; esters, such as ethyl acetate, propyl acetate, butyl acetate, methyl propionate, ethyl propionate, and butyl propionate; ketones, such as acetone, ethyl methyl ketone, and diethyl ketone; lactones, such as γ-butyrolactone, γ-valerolactone, tetrahydrofuran, and tetrahydropyran; ethers, such as diethyl ether, dibutyl ether, diisopropyl ether, 1,2-dimethoxyethane, 1,2-diethoxyethane, and tetrahydrofuran; nitriles, such as acetonitrile, propionitrile, and benzonitrile; amides, such as N,N-dimethylformamide; sulfones, such as dimethyl sulfoxide and sulfolane; and the like. These aqueous and non-aqueous solvents can be used singly or in combination of two or more. Of these, it is preferable to use solvents that have a high boiling point and that do not easily decompose bases, described later. Specifically, a non-aqueous solvent is preferable, ether is more preferable, and dibutyl ether is particularly preferable.

Base

When the step of subjecting the halogenated butane compound to a dehydrofluorination reaction in the present disclosure is performed in the liquid phase, this step is preferably performed in the presence of a base, as described above.

From the viewpoint of the conversion rate of the reaction and the selectivity and yield of the halogenated butene compound, the base is preferably a hydroxide or alkoxide of an alkali metal or alkaline earth metal, and more preferably an alkoxide of an alkali metal or alkaline earth metal. Specific examples include sodium hydroxide, potassium hydroxide, sodium methoxide, potassium tert-butoxide, and the like; and preferably sodium methoxide, potassium tert-butoxide, and the like. In this step, it is preferable to use an aqueous solution of a hydroxide or alkoxide of an alkali metal or alkaline earth metal, and more preferably an aqueous solution of an alkoxide of an alkali metal or alkaline earth metal. Specifically, an aqueous solution of sodium methoxide, potassium methoxide, potassium ethoxide, potassium tert-butoxide, or the like is particularly preferable. Due to the use of such a base, the target compound can be obtained at a higher selectivity and higher conversion rate.

The content of the base in the reaction solution is not limited, but is preferably 20 to 60 mass %, and more preferably 40 to 55 mass %, based on the entire reaction solution, which is taken as 100 mass %. When the content of the base in the reaction solution is within these ranges, the target compound can be obtained at a higher selectivity and higher conversion rate.

Catalyst

In this step, a catalyst can be used, if necessary. The catalyst used in this step is preferably a hydrocarbon-based alkoxide. Examples of hydrocarbon-based alkoxides include tetramethylammonium fluoride, tetramethylammonium chloride, tetramethylammonium bromide, tetramethylammonium iodide, tetraethylammonium fluoride, tetraethylammonium chloride, tetraethylammonium bromide, tetraethylammonium iodide, tetrapropylammonium fluoride, tetrapropylammonium chloride, tetrapropylammonium bromide, tetrapropylammonium iodide, tetrabutylammonium fluoride, tetrabutylammonium chloride, tetrabutylammonium bromide, tetrabutylammonium iodide, benzyltriethylammonium fluoride, benzyltriethylammonium chloride, benzyltriethylammonium bromide, benzyltriethylammonium iodide, benzyltributylammonium fluoride, benzyltributylammonium chloride, benzyltributylammonium bromide, benzyltributylammonium iodide, methyltributylammonium fluoride, methyltributylammonium chloride, methyltributylammonium bromide, methyltributylammonium iodide, methyltrioctylammonium fluoride, methyltrioctylammonium chloride (trademark: Aliquat 336), methyltrioctylammonium bromide, methyltrioctylammonium iodide, and the like. The catalysts can be used singly or in combination of two or more. Due to the use of such a catalyst, the target compound can be obtained at a higher selectivity and higher conversion rate.

Cyclic Halogen Carbide Compound

In the present disclosure, the step of subjecting the halogenated butane compound to a dehydrofluorination reaction can be performed in the presence of a cyclic halogen carbide compound. The cyclic halogen carbide compound refers to a cyclic halogen carbide compound in which all hydrogen atoms bonded to carbon atoms in a hydrocarbon compound are replaced by halogen atoms. In other words, this compound refers to a cyclic halogen carbide compound consisting of carbon atoms and halogen atoms and containing no hydrogen atoms.

When the step of subjecting the halogenated butane compound to a dehydrofluorination reaction is performed in the presence of such a cyclic halogen carbide compound, it is possible to shift the equilibrium of the reaction to the product side, and a halogenated butene compound, which is the target product, can be obtained at a higher conversion rate and higher yield.

Examples of the halogen atom in the usable cyclic halogen carbide compound include any of fluorine atoms, chlorine atoms, bromine atoms, and iodine atoms. Of these, from the viewpoint of reaction efficiency, it is preferable to contain the same type of halogen atom as the halogen atom ($X^1$, $X^2$, $X^3$, $X^4$, $X^5$, $X^6$, and $X^7$) contained in the halogenated butane compound, which is a raw material compound. When the halogenated butane compound has a plurality of halogen atoms (when not all of $X^1$, $X^2$, $X^3$, $X^4$, $X^5$, $X^6$, and $X^7$ are the same), it is preferable that the cyclic halogen carbide compound contains one or two or more of the halogen atoms contained in the halogenated butane compound, and more preferably one of the halogen atoms contained in the halogenated butane compound.

The number of carbon atoms in the usable cyclic halogen carbide compound is not limited. From the viewpoint of the conversion rate, selectivity, and yield of the halogenated butene compound as the target product, the number of carbon atoms in the cyclic halogen carbide compound is preferably 1 to 10, more preferably 2 to 7, and even more preferably 3 to 5.

The usable cyclic halogen carbide compound may be a saturated cyclic halogen carbide compound without an unsaturated bond or an unsaturated cyclic halogen carbide compound with an unsaturated bond. Of these, a saturated cyclic halogen carbide compound is preferred from the viewpoint of the conversion rate, selectivity, and yield of the halogenated butene compound as the target product.

From the above, the cyclic halogen carbide compound is preferably a saturated cyclic halogen carbide compound. Such a saturated cyclic halogen carbide compound is preferably a saturated cyclic halogen carbide compound represented by formula (4):

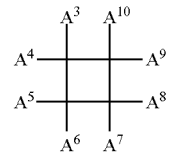

(4)

wherein $A^3$, $A^4$, $A^5$, $A^6$, $A^7$, $A^8$, $A^9$, and $A^{10}$ are the same or different and each is a fluorine atom or a perfluoroalkyl group.

In formula (4), the perfluoroalkyl group represented by $A^3$, $A^4$, $A^5$, $A^6$, $A^7$, $A^8$, $A^9$, and $A^{10}$ refers to an alkyl group in which all of the hydrogen atoms are replaced by fluorine atoms. Such a perfluoroalkyl group is, for example, a perfluoroalkyl group having 1 to 20 carbon atoms, preferably 1 to 12 carbon atoms, more preferably 1 to 6 carbon atoms, even more preferably 1 to 4 carbon atoms, and particularly preferably 1 to 3 carbon atoms. The perfluoroalkyl group is preferably a linear or branched perfluoroalkyl group. Such a perfluoroalkyl group is preferably a trifluoromethyl group ($CF_3$—) or a pentafluoroethyl group ($C_2F_5$—).

Specific examples of the cyclic halogen carbide compound that satisfies the above conditions include:

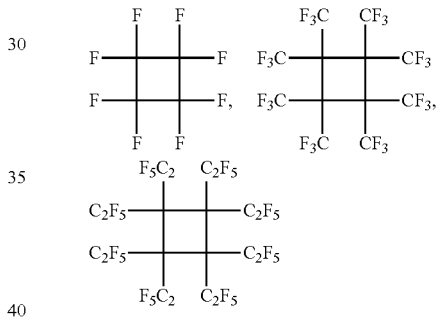

In the production method of the present disclosure, when the halogenated butane compound is subjected to a dehydrofluorination reaction in the liquid phase in the presence of a cyclic halogen carbide compound, for example, the cyclic halogen carbide compound may be blown in a gaseous state into a solution of the halogenated butane compound, or a liquid phase (e.g., liquefied gas) may be supplied thereinto.

In the production method of the present disclosure, when the halogenated butane compound is subjected to a dehydrofluorination reaction in the presence of a cyclic halogen carbide compound, the amount of the cyclic halogen carbide compound used is not limited. From the viewpoint of the conversion rate, selectivity, and yield of the halogenated butene compound as the target product, the amount of the cyclic halogen carbide compound is preferably an excessive amount based on the halogenated butane compound, which is a raw material compound, and specifically preferably 1 to 20 mol, more preferably 2 to 10 mol, and even more preferably 3 to 5 mol, per mol of the halogenated butane compound, which is a raw material compound.

Closed Reaction Process

In the present disclosure, the halogenated butene compound represented by formula (2A) as the target compound has a low boiling point and exists as a gas at room temperature. Accordingly, in the step of performing a dehydrofluorination reaction in the present disclosure, when a closed reaction process is used as the reaction system, the pressure inside the closed reaction process naturally rises, and the reaction can be carried out under pressurized conditions. Therefore, the halogenated butene compound represented by formula (2A) as the target compound can be obtained at a higher selectivity and higher conversion rate.

Thus, the closed reaction process is pressurized due to the low boiling point of the target compound, and the concentration of the substrate (raw material compound) in the reaction solution (base solution) increases, which can improve the reactivity. In the closed reaction process, it is preferable to carry out the reaction while sealing the reaction system using a batch-type pressure-resistant reaction vessel. When the reaction is carried out in a batch process, it is preferable, for example, to place a raw material compound, a base solution (alkaline aqueous solution), a catalyst, etc., in a pressure vessel, such as an autoclave, raise the temperature to an appropriate reaction temperature with a heater, and carry out the reaction while stirring for a certain period of time. As the reaction atmosphere, it is preferable to carry out the reaction in an inert gas atmosphere, such as nitrogen, helium, or carbon dioxide.

In the step of performing a dehydrofluorination reaction in the present disclosure, the reaction temperature in the closed reaction process is generally preferably 0° C. or higher, more preferably 10° C. or higher, and even more preferably 15° C. or higher, from the viewpoint that the elimination reaction can proceed more efficiently and the target compound can be obtained at a higher selectivity, and from the viewpoint of suppressing the decrease in the conversion rate.

In the step of performing a dehydrofluorination reaction in the present disclosure, the reaction temperature in the closed reaction process is generally preferably 100° C. or lower, and more preferably 80° C. or lower, from the viewpoint that the dehydrofluorination reaction can proceed more efficiently and the target compound can be obtained at a higher selectivity, and from the viewpoint of further suppressing the decrease in selectivity due to the decomposition or polymerization of the reaction product.

Pressure-Increased Reaction Process

In the step of performing a dehydrofluorination reaction in the present disclosure, the reaction can be carried out in a pressure-increased reaction process by setting the reaction temperature to 10° C. or higher and the reaction pressure to 0 kPa or more. As a result, the halogenated butene compound represented by formula (2A) as the target compound can be obtained at a higher selectivity and higher conversion rate. When the reaction system is pressurized in this way, the concentration of the substrate (raw material compound) in the reaction solution (base solution, alkaline aqueous solution) rises, which can improve the reactivity. In the pressure-increased reaction process, it is preferable to carry out the reaction while sealing the reaction system using a batch-type pressure-resistant reaction vessel. When the reaction is carried out in a batch process, it is preferable, for example, to place a raw material compound, a base solution (alkaline aqueous solution), a catalyst, etc., in a pressure vessel, such as an autoclave, raise the temperature to an appropriate reaction temperature with a heater, and carry out the reaction while stirring for a certain period of time.

In the step of performing an elimination reaction in the present disclosure, the pressurizing condition is preferably such that the reaction pressure is 0 kPa or more. The reaction pressure is the pressure inside the reaction vessel used for the pressure-increased reaction process. In the step of performing a dehydrofluorination reaction in the present disclosure, the reaction pressure is preferably 0 kPa or more, more preferably 5 kPa or more, even more preferably 10 kPa or more, and particularly preferably 15 kPa or more. The upper limit of the reaction pressure is not limited, and is generally about 2 MPa. In the present disclosure, the pressure is gauge pressure unless otherwise specified.

For pressurization, the pressure in the reaction system can be increased by sending an inert gas, such as nitrogen, helium, or carbon dioxide, into the reaction system.

In the step of performing a dehydrofluorination reaction in the present disclosure, the reaction temperature in the pressure-increased reaction process is generally preferably 0° C. or higher, more preferably 10° C. or higher, and even more preferably 15° C. or higher, from the viewpoint that the elimination reaction can proceed more efficiently and the target compound can be obtained at a higher selectivity, and from the viewpoint of suppressing the decrease in the conversion rate.

In the step of performing a dehydrofluorination reaction in the present disclosure, the reaction temperature in the closed reaction process is generally preferably 100° C. or lower, and more preferably 80° C. or lower, from the viewpoint that the dehydrofluorination reaction can proceed more efficiently and the target compound can be obtained at a higher selectivity, and from the viewpoint of further suppressing the decrease in selectivity due to the decomposition or polymerization of the reaction product.

Combination of Closed Reaction Process and Pressure-Increased Reaction Process

In the step of performing a dehydrofluorination reaction in the present disclosure, it is also possible to carry out the reaction in a continuous and pressurized reaction form, while extracting the liquid or extracting the gasified product, by connecting a back pressure valve to a continuous stirred-tank reactor (CSTR).

After the dehydrofluorination reaction is completed, purification can be optionally performed according to a conventional method, thereby obtaining a halogenated butene compound represented by formula (2A).

(1-1-2-2) Gas-Phase Reaction

When the step of subjecting the halogenated butane compound to a dehydrofluorination reaction in the present disclosure is performed in the gas phase, it is advantageous in that the use of a solvent is not required, no industrial waste is generated, and productivity is excellent.

The step of subjecting the halogenated butane compound to a dehydrofluorination reaction in the present disclosure is preferably carried out in the gas phase, particularly by a gas-phase continuous flow process using a fixed bed reactor. When a gas-phase continuous flow process is used, the device, operation, etc. can be simplified, and it is economically advantageous.

Catalyst

The step of subjecting the halogenated butane compound to a dehydrofluorination reaction in the present disclosure is preferably performed in the presence of a catalyst.

Preferred examples of the catalyst used in the production method of the present disclosure include activated carbon catalysts, chromium oxide catalysts, zeolite catalysts, silica alumina catalysts, and the like. These catalysts can be both non-fluorinated catalysts and fluorinated catalysts.

Activated carbon catalysts are not limited, and examples include powdered activated carbon, such as crushed coal, formed coal, granulated coal, and spherical coal. As the powdered activated carbon, it is preferable to use powdered activated carbon that shows a particle size of 4 mesh (4.75 nm) to 100 mesh (0.150 mm) according to the JIS test (JIS Z8801). These activated carbons can be known or commercially available products.

Since activated carbon shows higher activity by fluorination, it is also possible to use, as an activated carbon catalyst, fluorinated activated carbon obtained by previously fluorinating activated carbon before use in the reaction. That is, non-fluorinated activated carbon and fluorinated activated carbon can both be used as the activated carbon catalyst.

Usable examples of fluorinating agents for fluorinating activated carbon include HF and like inorganic fluorinating agents, as well as hydrofluorocarbon (HFC) such as hexafluoropropene, chlorofluorocarbon (CFC) such as chlorofluoromethane, hydrochlorofluorocarbon (HCFC), and like organic fluorinating agents.

The method of fluorinating activated carbon is, for example, fluorination by circulating a fluorinating agent mentioned above at atmospheric pressure at a temperature of room temperature (25° C.) to about 400° C.

Chromium oxide catalysts are not limited; however, when chromium oxide is represented by CrOm, it is preferable to satisfy $1.5<m<3$, more preferably $2<m<2.75$, and even more preferably $2<m<2.3$. Further, when chromium oxide is represented by $CrO_m \cdot nH_2O$, it may be hydrated so that the value of n is 3 or less, particularly 1 to 1.5.

The fluorinated chromium oxide catalyst can be prepared by fluorinating a chromium oxide catalyst mentioned above. This fluorination can be carried out using, for example, HF or fluorocarbon. Such a fluorinated chromium oxide catalyst can be synthesized according to the method described in JPH05-146680A, for example.

The following is an example of a method for synthesizing a chromium oxide catalyst and a fluorinated chromium oxide catalyst.

First, a precipitate of chromium hydroxide can be obtained by mixing an aqueous solution of a chromium salt (chromium nitrate, chromium chloride, chromium alum, chromium sulfate, etc.) with aqueous ammonia. The physical properties of the chromium hydroxide can be controlled by the reaction rate of the precipitation reaction at this time. The reaction rate is preferably fast. The reaction rate depends on the reaction solution temperature, aqueous ammonia mixing method (mixing rate), stirring state, etc.

The precipitate can be filtered and washed, and then dried. Drying can be carried out, for example, in air at 70 to 200° C. for 1 to 100 hours. The catalyst at this stage is sometimes called the "state of chromium hydroxide." Then, this catalyst can be crushed. From the viewpoint of pellet strength, catalyst activity, etc., it is preferable to adjust the precipitation reaction rate so that the powder density of the crushed powder (e.g., 95% of powder having a particle size of 1000 μm or less, particularly 46 to 1000 μm) is 0.6 to 1.1 g/ml, and preferably 0.6 to 1.0 g/ml. The specific surface area of the powder (specific surface area by the BET method) is preferably 100 $m^2/g$ or more, and more preferably 120 $m^2/g$ or more, for example, under the degassing conditions at 200° C. for 80 minutes. The upper limit of the specific surface area is about 220 $m^2/g$, for example.

If necessary, this chromium hydroxide powder can be mixed with 3 wt % or less of graphite, and pellets can be formed with a tableting machine. The size and strength of the pellets can be adjusted as appropriate.

The formed catalyst can be calcined in an inert atmosphere (e.g., in a nitrogen stream) to give an amorphous chromium oxide. The calcination temperature is preferably 360° C. or higher, and preferably 380 to 460° C. from the viewpoint of suppressing crystallization. The calcination time can be set to 1 to 5 hours, for example.

The specific surface area of the calcined catalyst is preferably, for example, 170 mg or more, more preferably 180 $m^2/g$ or more, and even more preferably 200 $m^2/g$ or more, from the viewpoint of catalyst activity. The upper limit of the specific surface area is generally preferably about 240 $m^2/g$, and more preferably about 220 $m^2/g$.

Then, the chromium oxide can be fluorinated to obtain a fluorinated chromium oxide. The fluorination temperature may be in a temperature range in which the generated water is not condensed, and the upper limit may be a temperature at which the catalyst is not crystallized by the reaction heat. The fluorination temperature can be set to 100 to 460° C., for example. Although the pressure during fluorination is not limited, it is preferable to perform the fluorination at the pressure at the time of being subjected to the catalyst reaction.

As zeolite catalysts, known types of zeolite can be widely used. For example, crystalline hydrous aluminosilicates of alkali metals or alkaline earth metals are preferred. The crystal form of zeolite is not limited, and examples include A type, X type, LSX type, and the like. The alkali metal or alkali earth metal in zeolite is not limited, and examples include potassium, sodium, calcium, lithium, and the like.

Because the zeolite catalyst shows higher activity by fluorination, the zeolite catalyst can be previously fluorinated before use in the reaction and used as a fluorinated zeolite catalyst.

Usable examples of fluorinating agents for fluorinating zeolite catalysts include inorganic fluorinating agents, such as $F_2$ and HF; fluorocarbon-based organic fluorinating agents, such as hexafluoropropene; and the like.

The method for fluorinating the zeolite catalyst is, for example, fluorination by circulating a fluorinating agent mentioned above at atmospheric pressure at a temperature of room temperature (25° C.) to about 400° C.

The silica alumina catalyst is a composite oxide catalyst containing silica ($SiO_2$) and alumina ($Al_2O_3$). When the total amount of silica and alumina is taken as 100 mass %, the usable catalyst has, for example, a silica content of 20 to 90 mass %, and particularly 50 to 80 mass %.

Because the silica alumina catalyst shows higher activity by fluorination, the silica alumina catalyst can be previously fluorinated before use in the reaction and used as a fluorinated silica alumina catalyst.

Usable examples of fluorinating agents for fluorinating silica alumina catalysts include inorganic fluorinating agents, such as $F_2$ and HF; fluorocarbon-based organic fluorinating agents, such as hexafluoropropene; and the like.

The method for fluorinating the silica alumina catalyst is, for example, fluorination by circulating a fluorinating agent mentioned above at atmospheric pressure at a temperature of room temperature (25° C.) to about 400° C.

The above catalysts can be used singly or in combination of two or more. From the viewpoint of conversion rate, selectivity, and yield, preferred of these are activated carbon catalysts (activated carbon or fluorinated activated carbon), chromium oxide catalysts (chromium oxide or fluorinated chromium oxide), etc.; and more preferred are activated carbon catalysts (activated carbon or fluorinated activated carbon).

When the chromium oxide catalyst, zeolite catalyst, silica alumina catalyst, or the like mentioned above is used as the catalyst, it can also be supported on a carrier. Usable examples of such carriers include carbon, alumina ($Al_2O_3$), zirconia ($ZrO_2$), silica ($SiO_2$), titania ($TiO_2$), and the like. As the carbon, activated carbon, amorphous carbon, graphite, diamond, etc. can be used.

In the production method of the present disclosure, when the halogenated butane compound is subjected to a dehydrofluorination reaction in the gas phase in the presence of a catalyst, for example, it is preferable to bring the catalyst in a solid state (solid phase) into contact with the halogenated butane compound. In this case, the shape of the catalyst can be powder; however, the form of pellets is preferable when it is used for the reaction of the gas-phase continuous flow process.

The specific surface area (hereinafter also referred to as "BET specific surface area") of the catalyst measured by the BET method is generally preferably 10 to 3000 $m^2/g$, more preferably 10 to 2500 $m^2/g$, even more preferably 20 to 2000 $m^2/g$, and particularly preferably 30 to 1500 $m^2/g$. When the BET specific surface area of the catalyst is within these ranges, the particle density of the catalyst is not too low. Thus, the halogenated butene compound can be obtained at a higher selectivity. In addition, the conversion rate of the halogenated butane compound can be further improved.

Cyclic Halogen Carbide Compound

In the present disclosure, the steps of subjecting the halogenated butane compound to a dehydrofluorination reaction can also be performed in the presence of a cyclic halogen carbide compound. The cyclic halogen carbide compound refers to a cyclic halogen carbide compound in which all hydrogen atoms bonded to carbon atoms in a hydrocarbon compound are replaced by halogen atoms. In other words, this compound refers to a cyclic halogen carbide compound consisting of carbon atoms and halogen atoms and containing no hydrogen atoms.

When the step of subjecting the halogenated butane compound to a dehydrofluorination reaction is performed in the presence of such a cyclic halogen carbide compound, it is possible to shift the equilibrium of the reaction to the product side, and a halogenated butene compound, which is the target product, can be obtained at a higher conversion rate and higher yield.

As such a cyclic halogen carbide compound, those described in the "(1-1-2-1) Liquid-Phase Reaction" section above can be adopted. The same applies to preferred specific examples and amounts used.

In the production method of the present disclosure, when the halogenated butane compound is subjected to a dehydrofluorination reaction in the gas phase in the presence of a cyclic halogen carbide compound, for example, it is preferable to bring the cyclic halogen carbide compound in the form of gas (gas phase) into contact with the halogenated butane compound.

Reaction Temperature

In the step of subjecting the halogenated butane compound to a dehydrofluorination reaction in the present disclosure, the reaction temperature is generally preferably 230° C. or higher, more preferably 280° C. or higher, and even more preferably 320° C. or higher, from the viewpoint that the dehydrofluorination reaction can proceed more efficiently, the conversion rate can be further improved, and the halogenated butene compound as the target compound can be obtained at a higher selectivity. When activated carbon is used as the catalyst, and when a cyclic halogen carbide compound is not used, the reaction temperature is preferably higher in order to promote the dehydrofluorination reaction more effectively, and is preferably 400° C. or higher, and more preferably 420° C. or higher. Even when activated carbon is used as the catalyst, and when the halogenated butane compound is subjected to a dehydrofluorination reaction in the gas phase in the presence of a cyclic halogen carbide compound, the dehydrofluorination reaction can proceed more efficiently; thus, the reaction temperature can be set slightly lower, and is generally preferably 230° C. or higher, more preferably 280° C. or higher, and even more preferably 320° C. or higher.

The reaction temperature for subjecting the halogenated butane compound to a dehydrofluorination reaction in the present disclosure is generally preferably 500° C. or lower, and more preferably 450° C. or lower, from the viewpoint that the dehydrofluorination reaction can proceed more efficiently, the conversion rate can be further improved, and the halogenated butene compound as the target compound can be obtained at a higher selectivity.

Reaction Time

Regarding the reaction time for subjecting the halogenated butane compound to a dehydrofluorination reaction in the present disclosure, for example, when a gas phase flow process is used, the contact time of the raw material compound with the catalyst (W/F) [W: weight (g) of catalyst, F: flow rate (cc/sec) of raw material compound] is preferably 5 to 100 g·sec/cc, more preferably 10 to 90 g·sec/cc, and even more preferably 15 to 80 g·sec/cc, from the viewpoint that the conversion rate of the reaction is particularly high and a halogenated butane compound can be obtained with higher yield and higher selectivity. When the halogenated butane compound is subjected to a dehydrofluorination reaction in the gas phase in the presence of a cyclic halogen carbide compound, the dehydrofluorination reaction can proceed more efficiently; thus, the lower limit of the contact time can be further reduced, and the contact time is preferably 1 to 100 g·sec/cc, more preferably 2 to 90 g·sec/cc, and even more preferably 3 to 80 g·sec/cc. The contact time refers to the time of contact between the raw material compound and the catalyst.

Reaction Pressure

The reaction pressure for subjecting the halogenated butane compound to a dehydrofluorination reaction in the present disclosure is preferably 0 kPa or more, more preferably 10 kPa or more, even more preferably 20 kPa or more, and particularly preferably 30 kPa or more, from the viewpoint that the dehydrofluorination reaction can proceed more efficiently, the conversion rate can be further improved, and the halogenated butene compound as the target compound can be obtained at a higher selectivity. The upper limit of the reaction pressure is not limited, and is generally about 2 MPa. In the present disclosure, the pressure is gauge pressure unless otherwise specified.

In the dehydrofluorination reaction of the halogenated butane compound in the present disclosure, the reactor for reacting the halogenated butane compound and preferably a catalyst and a cyclic halogen carbide compound is not limited in its shape and structure as long as it can withstand the temperature and pressure described above. Examples of the reactor include a vertical reactor, a horizontal reactor, a multitubular reactor, and the like. Examples of the material of the reactor include glass, stainless steel, iron, nickel, iron-nickel alloys, and the like.

Examples of Dehydrofluorination Reaction

The dehydrofluorination reaction of the halogenated butane compound in the present disclosure can be carried out in a batch process or a flow process in which the halogenated butane compound as a raw material compound is continuously fed into the reactor and the halogenated butene compound as a target compound is continuously withdrawn from the reactor. If the halogenated butene compound as a target compound remains in the reactor, the elimination reaction can proceed further; thus, it is preferable to carry out the reaction in a flow process. The step of subjecting the halogenated butane compound to a dehydrofluorination reaction in the present disclosure is preferably carried out in the gas phase, particularly by a gas-phase continuous flow process using a fixed bed reactor. When a gas-phase continuous flow process is used, the device, operation, etc. can be simplified, and it is economically advantageous. When a batch process is used, it is also possible to use the closed reaction process or pressure-increased reaction process explained in the "Liquid-Phase Reaction" section above.

The atmosphere when subjecting the halogenated butane compound to a dehydrofluorination reaction in the present disclosure is preferably an inert gas atmosphere, a hydrogen fluoride gas atmosphere, or the like, from the viewpoint of suppressing the deterioration of the catalyst. Examples of the inert gas include nitrogen, helium, argon, and the like. Among these inert gases, nitrogen is preferable from the viewpoint of cost reduction. The concentration of the inert gas is preferably 0 to 50 mol % of the gas component introduced into the reactor.

After the dehydrofluorination reaction is completed, purification can be optionally performed according to a conventional method, thereby obtaining a halogenated butene compound represented by formula (2A).

(1-1-3) Target Compound (Halogenated Butene Compound)

The target compound of the present disclosure obtained in the above manner is a halogenated butene compound represented by formula (2A):

$$CX^1X^2X^3CX^4=CHCX^5X^6X^7 \quad (2A)$$

wherein $X^1$, $X^2$, $X^3$, $X^4$, $X^5$, $X^6$, and $X^7$ are the same or different and each is a halogen atom.

$X^1$, $X^2$, $X^3$, $X^4$, $X^5$, $X^6$, and $X^7$ in formula (2A) correspond to $X^1$, $X^2$, $X^3$, $X^4$, $X^5$, $X^6$, and $X^7$ in formula (1A), respectively. Accordingly, specific examples of the halogenated butene compound represented by formula (2A) to be produced include $CF_3CF=CHCF_3$, $CCl_3CCl=CHCCl_3$, $CBr_3CBr=CHCBr_3$, and the like. These compounds contain both Z- and E-isomers.

The thus-obtained halogenated butene compound can be effectively used for various applications, such as etching gases for forming cutting-edge microstructures in semiconductors, liquid crystals, etc., as well as cleaning gases, deposit gases, refrigerants, heat transfer media, and building blocks for organic synthesis. The deposit gas and the building block for organic synthesis are described later.

1-2: Method for Producing Halogenated Butyne Compound from Halogenated Butene Compound The method for producing a halogenated butyne compound of the present disclosure is a method for producing a halogenated butyne compound represented by formula (3A):

$$CX^1X^2X^3C\equiv CX^5X^6X^7 \quad (3A)$$

wherein $X^1$, $X^2$, $X^3$, $X^5$, $X^6$, and $X^7$ are the same or different and each is a halogen atom, the method comprising subjecting a halogenated butene compound represented by formula (2A):

$$CX^1X^2X^3CX^4=CHCX^5X^6X^7 \quad (2A)$$

wherein $X^1$, $X^2$, $X^3$, $X^5$, $X^6$, and $X^7$ are as defined above, and $X^4$ is a halogen atom, to a dehydrohalogenation reaction.

According to the present disclosure, when the halogenated butene compound represented by formula (2A) is subjected to a dehydrohalogenation reaction, the halogenated butyne compound represented by formula (3A) in which 1 mol of hydrogen halide is eliminated per mol of the halogenated butene compound represented by formula (2A) can be selectively obtained.

(1-2-1) Raw Material Compound (Halogenated Butene Compound)

The halogenated butene compound as a substrate that can be used in the production method of the present disclosure is, as described above, the halogenated butene compound represented by formula (2A):

$$CX^1X^2X^3CX^4=CHCX^5X^6X^7 \quad (2A)$$

wherein $X^1$, $X^2$, $X^3$, $X^4$, $X^5$, $X^6$, and $X^7$ are the same or different and each is a halogen atom, and corresponds to the target compound in the "1-1: Method for Producing Halogenated Butene Compound from Halogenated Butane Compound" section above.

In formula (2A), as the halogen atom represented by $X^1$, $X^2$, $X^3$, $X^4$, $X^5$, $X^6$, and $X^7$, those mentioned above can be used. The same applies to preferred types.

Specific examples of the halogenated butene compound as a substrate that satisfies the above conditions include $CF_3CF=CHCF_3$, $CCl_3CCl=CHCCl_3$, $CBr_3CBr=CHCBr_3$, and the like. These compounds contain both Z- and E-isomers. These halogenated butene compounds can be used singly or in combination of two or more. Such halogenated butene compounds can be known or commercially available products.

(1-2-2) Dehydrohalogenation Reaction

In the step of subjecting the halogenated butene compound to a dehydrohalogenation reaction in the present disclosure, for example, in the halogenated butene compound represented by formula (2A) as a substrate, $X^1$, $X^2$, $X^3$, $X^4$, $X^5$, $X^6$, and $X^7$ are more preferably fluorine atoms.

That is, this reaction is preferably a dehydrofluorination reaction according to the following reaction formula:

$$CF_3CF=CHCF_3 \rightarrow CF_3C\equiv CCF_3+HF$$

The step of subjecting the halogenated butene compound to a dehydrohalogenation reaction in the present disclosure can be performed in the liquid phase or gas phase. Particularly from the viewpoint of productivity, it is preferable to perform the step in the gas phase.

The step of subjecting the halogenated butene compound to a dehydrohalogenation reaction in the present disclosure is preferably performed in the presence of a catalyst and/or a base, from the viewpoint of obtaining the target compound at a higher selectivity and higher conversion rate. More specifically, when a liquid-phase reaction is employed, the step is preferably performed in the presence of a base and optionally a catalyst, and when a gas-phase reaction is employed, the step is preferably performed in the presence of a catalyst. For the details of the liquid-phase reaction (solvent, base, catalyst, cyclic halogen carbide compound, conditions of closed reaction process and pressure-increased reaction process, etc.), and the details of the gas-phase reaction (catalyst, cyclic halogen carbide compound, reaction temperature, reaction time, reaction pressure, etc.), the explanation in the "1-1: Method for Producing Halogenated Butene Compound from Halogenated Butane Compound" section above can be applied, except that the "reaction to obtain a halogenated butene compound from a halogenated butane compound by a dehydrofluorination reaction" is read as a "reaction to obtain a halogenated butyne compound from a halogenated butene compound by a dehydrohalogenation reaction." The same applies to preferred types and contents.

After the dehydrohalogenation reaction is completed, purification can be optionally performed according to a conventional method, thereby obtaining a halogenated butyne compound represented by formula (3A).

(1-2-3) Target Compound (Halogenated Butyne Compound)

The target compound of the present disclosure obtained in the above manner is a halogenated butyne compound represented by formula (3A):

$$CX^1X^2X^3C\equiv CCX^5X^6X^7 \quad (3A)$$

wherein $X^1$, $X^2$, $X^3$, $X^5$, $X^6$, and $X^7$ are the same or different and each is a halogen atom.

$X^1$, $X^2$, $X^3$, $X^5$, $X^6$, and $X^7$ in formula (3A) correspond to $X^1$, $X^2$, $X^3$, $X^5$, $X^6$, and $X^7$ in formula (2A), respectively. Therefore, specific examples of the halogenated butyne compound represented by formula (3A) to be produced include $CF_3C\equiv CCF_3$, $CCl_3C\equiv CCCl_3$, $CBr_3C\equiv CCBr_3$, and the like.

The thus-obtained halogenated butyne compound can be effectively used for various applications, such as etching gases for forming cutting-edge microstructures in semiconductors, liquid crystals, etc., as well as cleaning gases, deposit gases, refrigerants, heat transfer media, and building blocks for organic synthesis. The deposit gas and the building block for organic synthesis are described later.

1-3: Method for Producing Halogenated Butyne Compound from Halogenated Butane Compound Via Halogenated Butene Compound The method for producing a halogenated butyne compound of the present disclosure is a method for producing a halogenated butyne compound represented by formula (3A):

$$CX^1X^2X^3C\equiv CX^5X^6X^7 \quad (3A)$$

wherein $X^1$, $X^2$, $X^3$, $X^5$, $X^6$, and $X^7$ are the same or different and each is a halogen atom, the method comprising:

(IA) subjecting a halogenated butane compound represented by formula (1A):

$$CX^1X^2X^3CHX^4CFHCX^5X^6X^7 \quad (1A)$$

wherein $X^1$, $X^2$, $X^3$, $X^5$, $X^6$, and $X^7$ are as defined above, and $X^4$ is a halogen atom, to a dehydrofluorination reaction to produce a halogenated butene compound represented by formula (2A):

$$CX^1X^2X^3CX^4=CHCX^5X^6X^7 \quad (2A)$$

wherein $X^1$, $X^2$, $X^3$, $X^4$, $X^5$, $X^6$, and $X^7$ are as defined above;

(IIA) after step (IA), removing hydrogen fluoride; and (IIIA) after step (IIA), subjecting the obtained halogenated butene compound represented by formula (2A):

$$CX^1X^2X^3CX^4=CHCX^5X^6X^7 \quad (2A)$$

wherein $X^1$, $X^2$, $X^3$, $X^4$, $X^5$, $X^6$, and $X^7$ are as defined above, to a dehydrohalogenation reaction to produce the halogenated butyne compound represented by formula (3A):

$$CX^1X^2X^3C\equiv CCX^5X^6X^7 \quad (3A)$$

wherein $X^1$, $X^2$, $X^3$, $X^5$, $X^6$, and $X^7$ are as defined above.

(1-3-1) Step (IA)

In the method for producing a halogenated butyne compound of the present disclosure, the explanation in the "1-1: Method for Producing Halogenated Butene Compound from Halogenated Butane Compound" section above can be applied to step (IA) as it is.

(1-3-2) Step (IIA)

The method for producing a halogenated butyne compound of the present disclosure comprises subjecting a halogenated butane compound represented by formula (1A) to a dehydrofluorination reaction to produce a halogenated butene compound represented by formula (2A) (step (IA)), and then removing hydrogen fluoride from the mixture containing the halogenated butene compound and hydrogen fluoride (step (IIA)).

In the method for producing a halogenated butyne compound of the present disclosure, after step (IA), the hydrogen fluoride generated by the dehydrofluorination reaction in step (IA) is separated and/or removed, followed by the production of a halogenated butyne compound in next step (IIIA), whereby a halogenated butyne compound, which is a target compound, can be produced by dehydrofluorination at a high conversion rate (yield) and high selectivity.

Figure 2:
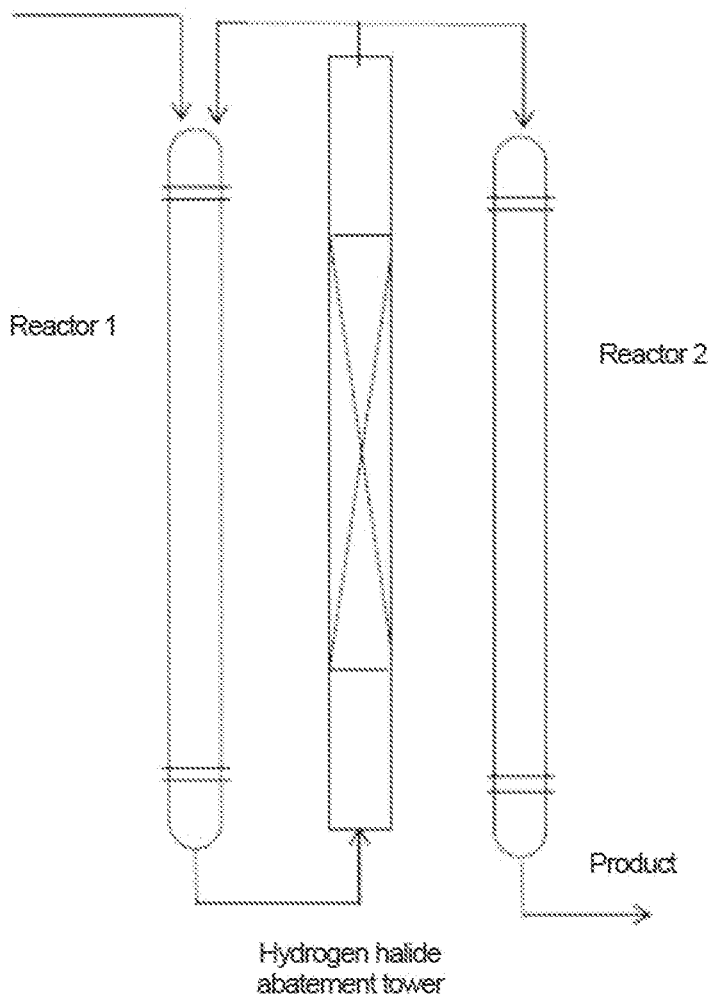
FIG. 2 is a view schematically showing a method for producing an alkene (halogenated butene compound or halogenated alkene compound) and an alkyne (halogenated butyne compound or fluorinated alkyne compound) in the present disclosure.

The hydrogen fluoride can be removed from the mixture containing the halogenated butene compound and hydrogen fluoride obtained in step (IA) preferably by separating the hydrogen fluoride in a rectification column (FIG. 1), or by removing the hydrogen fluoride using a hydrogen halide removal agent (removal column), such as alkali, Secard, aluminum, or silica (FIG. 2).

In the method for producing a halogenated butyne compound of the present disclosure, it is preferable to reuse the unreacted raw materials (halogenated butane compound, etc.) separated by rectification. In the method for producing a halogenated butyne compound of the present disclosure, the unreacted halogenated butane compound separated by rectification can be returned (reused) to the reactor and used for dehydrofluorination.

Method for Separating Hydrogen Fluoride in Rectification Column

The boiling point of the hydrogen fluoride (HF) to be separated is 19.54° C.

To remove hydrogen fluoride from the mixture containing the halogenated butene compound and hydrogen fluoride obtained in step (IA), the halogenated butene compound and the hydrogen fluoride are separated in a rectification column based on the boiling points of both compounds, and based on the difference in the boiling points of both compounds. Then, the halogenated butene compound is collected, and the hydrogen fluoride can be separated. In the production of a halogenated butyne compound in next step (IIIA), the hydrogen fluoride content can be reduced, and the halogenated butyne compound as the target compound can be produced at a high conversion rate (yield) and high selectivity.

Method for Removing Hydrogen Fluoride Using Hydrogen Halide Removal Agent

The hydrogen fluoride to be separated can be removed with a hydrogen fluoride removal agent. As the hydrogen fluoride removal agent, it is preferable to use alkali, alumina, silica, zeolite, Secard, and like hydrogen fluoride removal agents. Secard is an adsorbent (synthetic zeolite) that uses, as a main raw material, amorphous clay mineraloid (alumina/silica gel), which is called "allophane" and is composed of amorphous to poorly crystalline hydrous aluminum silicate.

To remove hydrogen fluoride from the mixture containing the halogenated butene compound and hydrogen fluoride obtained in step (IA), the hydrogen fluoride is removed using a hydrogen fluoride removal agent, and the halogenated butene compound can be collected. In the production of a halogenated butyne compound in next step (IIIA), the hydrogen fluoride content can be reduced, and the halogenated butyne compound as the target compound can be produced at a high conversion rate (yield) and high selectivity.

Concentration of Hydrogen Fluoride

In the method for producing a halogenated butyne compound of the present disclosure, after step (IA), the hydrogen fluoride generated by dehydrofluorination in step (IA) is separated and/or removed, followed by the production of a halogenated butyne compound in next step (IIIA), whereby a halogenated butyne compound, which is a target compound, can be produced by dehydrofluorination at a high conversion rate (yield) and high selectivity.

In the production of a halogenated butyne compound in next step (IIIA), the halogenated butene compound represented by formula (2A) is used as a raw material compound. In this case, in addition to the halogenated butene compound represented by formula (2A), the mixture containing hydrogen fluoride generated by dehydrofluorination may be brought into the production of a halogenated butyne compound in next step (IIIA).

In the method for producing a halogenated butyne compound of the present disclosure, from the viewpoint that in the production of a halogenated butyne compound in next step (IIIA), the halogenated butyne compound, which is a target compound, is produced by dehydrofluorination at a high conversion rate (yield) and high selectivity, in the composition used as a raw material in next step (IIIA), based on the mixture containing the halogenated butene compound represented by formula (2A) and hydrogen fluoride (100 mol %), the hydrogen fluoride content (concentration) is preferably 50 mol % or less, more preferably 20 mol % or less, even more preferably 3 mol % or less, and particularly preferably 0.1 mol % or less. When the mixture containing the halogenated butene compound represented by formula (2A) and hydrogen fluoride has a low hydrogen fluoride content, a halogenated butyne compound, which is a target compound, can be produced at a high conversion rate (yield) and high selectivity.

(1-3-3) Step (IIIA)

In the method for producing a halogenated butyne compound of the present disclosure, the explanation in the "1-2: Method for Producing Halogenated Butyne Compound from Halogenated Butene Compound" section above can be applied to step (IIIA) as it is.

(1-3-4) Examples of Dehydrofluorination

In the step of performing dehydrofluorination in the present disclosure, the reaction can be carried out in a batch process or a flow process in which the raw material compound (halogenated butane compound) is continuously fed into the reactor and the target compound (halogenated butene compound) is continuously withdrawn from the reactor in step (IA). Then, hydrogen fluoride is removed from the mixture containing the halogenated butene compound or hydrogen fluoride (step (IIA)). Step (IIIA) can be carried out in a batch process or a flow process in which the raw material compound (halogenated butene compound) is continuously fed into the reactor and the target compound (halogenated butyne compound) is continuously withdrawn from the reactor. In each step, the target compound (halogenated butene compound or halogenated butyne compound) does not remain in the reactor, and dehydrofluorination can further proceed; thus, it is preferable to carry out the reaction in a flow process.

In the step of performing dehydrofluorination in the present disclosure, the reaction is preferably carried out in the gas phase, particularly by a gas-phase continuous flow process using a fixed bed reactor. When a gas-phase continuous flow process is used, the device, operation, etc. can be simplified, and it is economically advantageous.

In the step of performing dehydrofluorination in the present disclosure, the atmosphere when performing the reaction is preferably an inert gas atmosphere, from the viewpoint of suppressing the deterioration of the catalyst (activated carbon, metal catalyst, etc.). In the present disclosure, the inert gas is preferably at least one member selected from the group consisting of nitrogen, helium, argon, and carbon dioxide. Among these inert gases, nitrogen is more preferable from the viewpoint of cost reduction. The concentration of the inert gas is preferably 0 to 50 mol % of the gas component introduced into the reactor.

In the step of performing dehydrofluorination in the present disclosure, after the reaction is completed, as described above, purification can be optionally performed according to a conventional method, thereby obtaining the target compound (halogenated butene compound or halogenated butyne compound).

2. Methods for Producing Halogenated Alkene Compound and Fluorinated Alkyne Compound 2-1: Method for Producing Halogenated Alkene Compound from Halogenated Alkane Compound The method for producing a halogenated alkene compound of the present disclosure is a method for producing a halogenated alkene compound represented by formula (2B):

$$CX^8A^1=CHA^2 \quad (2B)$$

wherein $A^1$ and $A^2$ are the same or different and each is a fluorine atom or a perfluoroalkyl group, and $X^8$ is a halogen atom, the method comprising subjecting a halogenated alkane compound represented by formula (1B):

$$CHX^8A^1CHX^9A^2 \quad (1B)$$

wherein $A^1$ and $A^2$ are as defined above, and $X^8$ and $X^9$ are the same or different and each is a halogen atom, to a dehydrohalogenation reaction in the presence of a catalyst in the gas phase.

According to the present disclosure, when the halogenated alkane compound represented by formula (1B) is subjected to a dehydrohalogenation reaction in the presence of a catalyst in the gas phase, a halogenated alkene compound represented by formula (2B) in which 1 mol of hydrogen halide is eliminated per mol of the halogenated alkane compound represented by formula (1B) can be selectively obtained. Moreover, the elimination reaction of hydrogen halide represented by $HX^8$ from the halogenated alkene compound represented by formula (2B) is unlikely to occur continuously. Further, according to the present disclosure, as the halogenated alkene compound represented by formula (2B), the E-isomer can be selectively synthesized among the geometric isomers. This effect is more pronounced when $A^1$ and $A^2$ are perfluoroalkyl groups. Since the α-carbon of trihalogenated methyl groups, such as a $CF_3$ group, becomes electron-deficient due to the electron attraction effect of the trihalogenated methyl groups, such as a $CF_3$ group, halogenated anions, such as fluorine anions, are less likely to desorb. As a result, halogenated butene is more likely to be produced, instead of halogenated butyne. Further, selective synthesis of the E-isomer is more pronounced when $A^1$ and $A^2$ are perfluoroalkyl groups. This is because the trans configuration is more energetically stable due to steric hindrance of the trihalogenated methyl groups, such as a $CF_3$ group.

(2-1-1) Raw Material Compound (Halogenated Alkane Compound)

In the present disclosure, the raw material compound in the method for producing a halogenated alkene compound form a halogenated alkane compound is a halogenated alkane compound represented by formula (1B):

$$CHX^8A^1CHX^9A^2 \quad (1B)$$

wherein $A^1$ and $A^2$ are the same or different and each is a fluorine atom or a perfluoroalkyl group, and $X^8$ and $X^9$ are the same or different and each is a halogen atom.

In formula (1B), as the perfluoroalkyl group represented by $A^1$ and $A^2$, and the halogen atom represented by $X^8$ and $X^9$, those mentioned above can be used. The same applies to preferred specific examples.

Examples of the halogenated alkane compound as the raw material compound that satisfies the above conditions include $CF_3CHClCHClCF_3$ (336mdd), $CF_3CHClCHFCl$, $CHFClCHFCl$, $CF_3CHFCHFCF_3$ (338mee), $CF_3CHFCHF_2$, $CHF_2CHF_2$, $CF_3CHClCHClC_2F_5$, $C_2F_5CHClCHClC_2F_5$, $C_2F_5CHClCHFCl$, $CF_3CHFCHFC_2F_5$, $C_2F_5CHFCHFC_2F_5$, $C_2F_5CHFCHF_2$, and the like. These halogenated alkane compounds can be used singly or in combination of two or more. Such halogenated alkane compounds can be known or commercially available products.

(2-1-2) Dehydrohalogenation Reaction

In the step of subjecting the halogenated alkane compound to a dehydrohalogenation reaction in the present disclosure, in terms of capable of producing a halogenated alkene compound from the halogenated alkane compound at a high conversion rate (yield) and high selectivity, for example, in the halogenated alkane compound represented by formula (1B) as a substrate, $A^1$ and $A^2$ are preferably both trifluoromethyl groups ($CF_3$—), and $X^8$ and $X^9$ are more preferably fluorine atoms or chlorine atoms.

That is, this reaction is preferably a dehydrofluorination reaction or a dehydrochlorination reaction according to the following reaction formulas:

$$CF_3CHClCHClCF_3 \text{ (336}mdd\text{)} \rightarrow CF_3CCl=CHCF_3$$
$$((Z) \text{ or } (E)\text{-1326}mxz)+HCl$$

$$CF_3CHFCHFCF_3 \text{ (338}mee\text{)} \rightarrow CF_3CF=CHCF_3 \text{ ((Z)}$$
$$\text{or } (E)\text{-1327}myz)+HF$$

Catalyst

The step of subjecting the halogenated alkane compound to a dehydrohalogenation reaction to produce a halogenated alkene compound in the present disclosure is performed in the presence of a catalyst in the gas phase.

The catalyst used in this step is preferably at least one member selected from the group consisting of activated carbon and a metal catalyst, from the viewpoint of conversion rate, selectivity, and yield.

When a metal catalyst is used as the catalyst used in this step, the metal catalyst is preferably at least one member selected from the group consisting of chromium oxide, fluorinated chromium oxide, chromium fluoride, aluminum oxide, fluorinated aluminum oxide, aluminum fluoride, iron oxide, fluorinated iron oxide, iron fluoride, nickel oxide, fluorinated nickel oxide, nickel fluoride, magnesium oxide, fluorinated magnesium oxide, and magnesium fluoride.

In this step, in terms of capable of reacting the halogenated alkane compound as a raw material compound at a high conversion rate (yield), and producing a halogenated alkene compound as a target compound at a high selectivity, more preferred of these catalysts are activated carbon, chromium oxide, fluorinated chromium oxide, aluminum oxide, fluorinated aluminum oxide, etc.

In this step, when the raw material compound is brought into contact with a catalyst in the gas phase, it is preferable to bring the catalyst in a solid state (solid phase) into contact with the raw material compound.

In this step, the catalyst may be in powder form; however, the form of pellets is preferable for the reaction of the gas-phase continuous flow process.

The specific surface area (hereinafter also referred to as "BET specific surface area") of the catalyst measured by the BET method is generally preferably 10 to 3000 n/g, more preferably 100 to 2000 m$^2$/g, even more preferably 500 to 1500 m$^2$/g, and particularly preferably 1000 to 1300 m$^2$/g. When the BET specific surface area of the catalyst is within this range, the particle density of the catalyst is not too low. Thus, the target compound can be obtained at a higher selectivity. In addition, the conversion rate of the raw material compound can be further improved.

When activated carbon is used as the catalyst, it is preferable to use powdered activated carbon, such as crushed coal, formed coal, granulated coal, and spherical coal. As the powdered activated carbon, it is preferable to use powdered activated carbon that shows a particle size of 4 mesh (4.76 mm) to 100 mesh (0.149 nm) according to the JIS test.

When activated carbon is used as the catalyst, as the shape of the activated carbon (e.g., specific surface area: about 1200 m$^2$/g), it is preferable to use either powdered or granular activated carbon, and it is more preferable to use granular activated carbon.

When a metal catalyst is used as the catalyst, it is preferably supported on a carrier. As the carrier, for example, carbon, alumina ($Al_2O_3$), zirconia ($ZrO_2$), silica ($SiO_2$), titania ($TiO_2$), and the like can be preferably used. Further, as the carbon, activated carbon, amorphous carbon, graphite, diamond, and the like can be preferably used.

Chromium oxide and fluorinated chromium oxide are described as examples of the catalyst in the present disclosure. For example, when chromium oxide is represented by $Cr_2O_3 \cdot nH_2O$, the value of n is preferably 3 or less, and more preferably 1 to 1.5. Further, it is preferable for the chromium oxide that in composition formula: $CrO_m$, m generally satisfies 1.5<m<3. As the catalyst, fluorinated chromium oxide can be prepared by fluorinating chromium oxide. Examples of the fluorination include fluorination with hydrogen fluoride (HF), and fluorination with fluorocarbon etc.

Chromium oxide as the catalyst can be obtained according to the method described in JP3412165B, for example. Chromium oxide can be fluorinated with hydrogen fluoride (HF treatment) to obtain fluorinated chromium oxide. The fluorination temperature is preferably 100° C. to 460° C., for example. The fluorination pressure is preferably the pressure at the time of being subjected to the catalyst reaction. In the present disclosure, it is particularly preferable to use a highly fluorinated chromium oxide catalyst with a high fluorine content. The highly fluorinated chromium oxide catalyst can be obtained by fluorinating chromium oxide at a higher temperature than usual for a long period of time.

The highly fluorinated chromium oxide catalyst preferably has a fluorine content of 30 mass % or more, and more preferably 30 mass % to 45 mass %. The fluorine content can be measured by the mass change of the catalyst or by a general quantitative analysis method of chromium oxide.

Cyclic Halogen Carbide Compound

In the present disclosure, the step of subjecting the halogenated alkane compound to a dehydrohalogenation reaction can be performed in the presence of a cyclic halogen carbide compound. The cyclic halogen carbide compound refers to a cyclic halogen carbide compound in which all hydrogen atoms bonded to carbon atoms in a hydrocarbon compound are replaced by halogen atoms. In other words, this compound refers to a cyclic halogen carbide compound consisting of carbon atoms and halogen atoms and containing no hydrogen atoms.

When the step of subjecting the halogenated alkane compound to a dehydrohalogenation reaction is performed in the presence of such a cyclic halogen carbide compound, a halogenated alkene compound as the target product can be obtained at a higher conversion rate and higher yield.

As the cyclic halogen carbide compound, those mentioned above can be used. The same applies to preferred specific examples, amounts used, introduction methods in the liquid-phase reaction and gas-phase reaction, and the like.

Reaction Temperature

In the step of performing a dehydrohalogenation reaction in the present disclosure, the lower limit of the reaction temperature is generally 50° C., preferably 70° C., and more preferably 100° C., from the viewpoint of promoting the dehydrohalogenation reaction more efficiently, and obtaining the target compound (halogenated alkene compound) at a higher selectivity, and from the viewpoint of suppressing the decrease in the conversion rate from the raw material compound (halogenated alkane compound).

In the step of performing a dehydrohalogenation reaction in the present disclosure, the upper limit of the reaction temperature is generally 500° C., preferably 450° C., and more preferably 400° C., from the viewpoint that the dehydrohalogenation reaction can proceed more effectively, and the target compound (halogenated alkene compound) can be obtained at a higher selectivity, and from the viewpoint of suppressing the decrease in selectivity due to the decomposition or polymerization of the reaction product.

Reaction Time

In the step of performing a dehydrohalogenation reaction in the present disclosure, regarding the reaction time, if the contact time of the raw material compound with the catalyst ($W/F_0$) [W: weight (g) of catalyst, $F_0$: flow rate (cc/sec) of raw material compound] is longer, the conversion rate of the raw material compound can be increased; however, the amount of the catalyst increases and large equipment is required, which is inefficient.

Accordingly, in the step of performing a dehydrohalogenation reaction in the present disclosure, regarding the reaction time, the contact time ($W/F_L$) of the raw material compound (halogenated alkane compound) with the catalyst is preferably 0.1 to 200 g·sec/cc, more preferably 0.2 to 150 g·sec/cc, even more preferably 0.4 to 100 g·sec/cc, and particularly preferably 0.5 to 50 g·sec/cc, in terms of improving the conversion rate of the raw material compound (halogenated alkane compound) and suppressing equipment cost.

The contact time of the raw material compound with the catalyst refers to the time of contact between the raw material compound and the catalyst.

When the dehydrohalogenation reaction of the present disclosure is performed in the presence of a catalyst in the gas phase, the target compound (halogenated alkene compound) can be obtained at a higher selectivity particularly by appropriately adjusting the reaction temperature and reaction time (contact time) according to the catalyst.

In the dehydrohalogenation reaction of the present disclosure, when chromium oxide is used as the catalyst, the reaction temperature is preferably 300° C. or higher, and more preferably 350° C. or higher. Further, the contact time is preferably 10 g·sec/cc or more, more preferably 20 g·sec/cc or more, and even more preferably 40 g·sec/cc or more.

In the dehydrohalogenation reaction of the present disclosure, when alumina is used as the catalyst, the reaction temperature is preferably 300° C. or higher, and the contact time is preferably 5 g·sec/cc or more.

In the dehydrohalogenation reaction of the present disclosure, when activated carbon is used as the catalyst, the reaction temperature is preferably 50 to 600° C., and more preferably 100 to 400° C. Further, the contact time is preferably 0.2 to 100 g·sec/cc, more preferably 0.3 to 50 g·sec/cc, and even more preferably 0.5 to 43 g·sec/cc.

Reaction Pressure

In the step of performing a dehydrohalogenation reaction in the present disclosure, the reaction pressure is preferably −0.05 to 2 MPa, more preferably −0.01 to 1 MPa, and even more preferably normal pressure to 0.5 MPa, in terms of promoting the dehydrohalogenation reaction more efficiently. In the present disclosure, the pressure is gauge pressure unless otherwise specified.

In the step of performing a dehydrohalogenation reaction in the present disclosure, the reactor for reacting the raw material compound (halogenated alkane compound) and a catalyst (activated carbon, metal catalyst, etc.) by bringing them into contact with each other is not limited in its shape and structure as long as it can withstand the temperature and pressure described above. Examples of the reactor include a vertical reactor, a horizontal reactor, a multitubular reactor, and the like. Examples of the material of the reactor include glass, stainless steel, iron, nickel, iron-nickel alloys, and the like.

Examples of Dehydrohalogenation Reaction

The step of performing a dehydrohalogenation reaction in the present disclosure can be carried out in a batch process or a flow process in which the raw material compound (halogenated alkane compound) is continuously fed into the reactor and the target compound (halogenated alkene compound) is continuously withdrawn from the reactor. The target compound (halogenated alkene compound) does not remain in the reactor, and the dehydrohalogenation reaction can further proceed; thus, it is preferable to carry out the reaction in a flow process.

The step of performing a dehydrohalogenation reaction in the present disclosure is preferably carried out in the gas phase, particularly by a gas-phase continuous flow process using a fixed bed reactor. When a gas-phase continuous flow process is used, the device, operation, etc. can be simplified, and it is economically advantageous.

In the step of performing a dehydrohalogenation reaction in the present disclosure, the atmosphere when performing the reaction is preferably an inert gas atmosphere, from the viewpoint of suppressing the deterioration of the catalyst (activated carbon, metal catalyst, etc.). In the present disclosure, the inert gas is preferably at least one member selected from the group consisting of nitrogen, helium, argon, and carbon dioxide. Among these inert gases, nitrogen is more preferable from the viewpoint of cost reduction. The concentration of the inert gas is preferably 0 to 50 mol % of the gas component introduced into the reactor.

In the step of performing a dehydrohalogenation reaction in the present disclosure, after the reaction is completed, purification can be optionally performed according to a conventional method, thereby obtaining a halogenated alkene compound represented by formula (2B), which is a target compound.

(2-1-3) Target Compound (Halogenated Alkene Compound)

The target compound of the present disclosure obtained in the above manner is a halogenated alkene compound represented by formula (2B):

$$CX^8A^1=CHA^2 \quad (2B)$$

wherein $A^1$ and $A^2$ are the same or different and each is a fluorine atom or a perfluoroalkyl group, and $X^8$ is a halogen atom.

$A^1$, $A^2$, and $X^8$ in formula (2B) correspond to $A^1$, $A^2$, and $X^8$ in formula (1B), respectively. Therefore, specific examples of the halogenated alkene compound represented by formula (2B) to be produced include $CF_3CCl=CHCF_3$ ((Z) or (E)-1326mxz), $CF_3CCl=CHF$, $CF_3CCl=CHF$, $CF_3CF=CHCF_3$ ((Z) or (E)-1327myz), $CF_3CF=CHF$, $CF_2=CHF$, $CF_3CCl=CHC_2F_5$, $C_2F_5CCl=CHC_2F_5$, $C_2F_5CCl=CHF$, $CF_3CF=CHC_2F_5$, $C_2F_5CF=CHC_2F_5$, $C_2F_5CF=CHF$, and the like. These compounds contain both Z- and E-isomers.

The thus-obtained halogenated alkene compound can be effectively used for various applications, such as etching gases for forming cutting-edge microstructures in semiconductors, liquid crystals, etc., as well as cleaning gases, deposit gases, refrigerants, heat transfer media, and building blocks for organic synthesis. The deposit gas and the building block for organic synthesis are described later.

2-2: Method for Producing Fluorinated Alkyne Compound from Halogenated Alkene Compound The method for producing a fluorinated alkyne compound of the present disclosure is a method for producing a fluorinated alkyne compound represented by formula (3B):

$$CA^1 \equiv CA^2 \quad (3B)$$

wherein $A^1$ and $A^2$ are the same or different and each is a fluorine atom or a perfluoroalkyl group, the method comprising subjecting a halogenated alkene compound represented by formula (2B):

$$CX^8A^1=CHA^2 \quad (2B)$$

wherein $A^1$ and $A^2$ are as defined above, and $X^8$ is a halogen atom, to a dehydrohalogenation reaction in the presence of a catalyst.

(2-2-1) Raw Material Compound (Halogenated Alkene Compound)

The halogenated alkene compound as a substrate that can be used in the production method of the present disclosure is, as described above, a halogenated alkene compound represented by formula (2B):

$$CX^8A^1=CHA^2 \quad (2B)$$

wherein $A^1$ and $A^2$ are the same or different and each is a fluorine atom or a perfluoroalkyl group, and $X^8$ is a halogen atom. This compound corresponds to the target compound in the "2-1: Method for Producing Halogenated Alkene Compound from Halogenated Alkane Compound" section above.

In formula (2B), as the perfluoroalkyl group represented by $A^1$ and $A^2$, and the halogen atom represented by $X^8$, those mentioned above can be used. The same applies to preferred types.

Specific examples of the halogenated alkene compound as a substrate that satisfies the above conditions include $CF_3CCl=CHCF_3$ ((Z) or (E)-1326mxz), $CF_3CCl=CHF$, $CFCl=CHF$, $CF_3CF=CHCF_3$ ((Z) or (E)-1327myz), $CF_3CF=CHF$, $CF_3=CHF$, $CF_3CCl=CHC_2F_5$, $C_2F_5CCl=CHC_2F_5$, $C_2F_5CCl=CHF$, $CF_3CF=CHC_2F_5$, $C_2F_5CF=CHC_2F_5$, $C_2F_5CF=CHF$, and the like. These compounds contain both Z- and E-isomers. These halogenated alkene compounds can be used singly or in combination of two or more. Such halogenated alkene compounds can be known or commercially available products.

(2-2-2) Dehydrohalogenation Reaction

In the step of subjecting the halogenated alkene compound to a dehydrohalogenation reaction in the present disclosure, in terms of capable of producing a fluorinated alkyne compound from the halogenated alkene compound at a high conversion rate (yield) and high selectivity, for example, in the halogenated alkene compound represented by formula (2B) as a substrate, $A^1$ and $A^2$ are preferably both trifluoromethyl groups ($CF_3$—), and $X^8$ is more preferably a fluorine atom or a chlorine atom.

That is, this reaction is preferably a dehydrofluorination reaction or a dehydrochlorination reaction according to the following reaction formulas:

$CF_3CCl=CHCF_3$ ((Z) or (E)-1326mxz)
→$CF_3C\equiv CCF_3$ (PF2B)+HCl $CF_3CF=CHCF_3$ ((Z) or (E)-1327myz)→$CF_3C\equiv CF_3$ (PF2B)+HF The step of subjecting the halogenated alkene compound to a dehydrohalogenation reaction in the present disclosure can be performed in the liquid phase or gas phase. Particularly from the viewpoint of productivity, it is preferable to perform the step in the gas phase.

The step of subjecting the halogenated alkene compound to a dehydrohalogenation reaction in the present disclosure is preferably performed in the presence of a catalyst and/or a base, from the viewpoint of obtaining the target compound at a higher selectivity and higher conversion rate. More specifically, when a liquid-phase reaction is employed, the step is preferably performed in the presence of a base and optionally a catalyst, and when a gas-phase reaction is employed, the step is preferably performed in the presence of a catalyst. For the details of the liquid-phase reaction (solvent, base, catalyst, cyclic halogen carbide compound, conditions of closed reaction process and pressure-increased reaction process, etc.), the explanation in the "1-1: Method for Producing Halogenated Butene Compound from Halogenated Butane Compound" section above can be applied, except that the "reaction to obtain a halogenated butene compound from a halogenated butane compound by a dehydrofluorination reaction" is read as a "reaction to obtain a fluorinated alkyne compound from a halogenated alkene compound by a dehydrohalogenation reaction." Further, for the details of the gas-phase reaction (catalyst, cyclic halogen carbide compound, reaction temperature, reaction time, reaction pressure, etc.), the explanation in the "2-1: Method for Producing Halogenated Alkene Compound from Halogenated Alkane Compound" section above can be applied, except that the "reaction to obtain a halogenated alkene compound from a halogenated alkane compound by a dehydrohalogenation reaction" is read as a "reaction to obtain a fluorinated alkyne compound from a halogenated alkene compound by a dehydrohalogenation reaction." The same applies to preferred types and contents.

After the dehydrohalogenation reaction is completed, purification can be optionally performed according to a conventional method, thereby obtaining a fluorinated butyne compound represented by formula (3B).

(2-2-3) Target Compound (Fluorinated Butyne Compound)

The target compound of the present disclosure obtained in the above manner is a fluorinated butyne compound represented by formula (3B):

$$CA^1 \equiv CA^2 \quad (3B)$$

wherein $A^1$ and $A^2$ are the same or different and each is a fluorine atom or a perfluoroalkyl group.

$A^1$ and $A^2$ in formula (3B) correspond to $A^1$ and $A^2$ in formula (2B), respectively. Accordingly, specific examples of the fluorinated butyne compound represented by formula (3B) to be produced include $CF_3C\equiv CCF_3$ (PF2B), $CF_3C\equiv CF$, $CF\equiv CF$, $CF_3C\equiv CC_2F_5$, $C_2F_5C\equiv CC_2F_5$, $C_2F_5C\equiv CF$, and the like.

The thus-obtained fluorinated butyne compound can be effectively used for various applications, such as etching gases for forming cutting-edge microstructures in semiconductors, liquid crystals, etc., as well as cleaning gases, deposit gases, refrigerants, heat transfer media, and building blocks for organic synthesis. The deposit gas and the building block for organic synthesis are described later.

2-3: Method for Producing Fluorinated Alkyne Compound from Halogenated Alkane Compound Via Halogenated Alkene Compound The method for producing a fluorinated alkyne compound of the present disclosure is a method for producing a fluorinated alkyne compound represented by formula (3B):

$$CA^1\equiv CA^2 \quad (3B)$$

wherein $A^1$ and $A^2$ are the same or different and each is a fluorine atom or a perfluoroalkyl group, the method comprising:

(IB) subjecting a halogenated alkane compound represented by formula (1B):

$$CHX^8A^1CHX^9A^2 \quad (1B)$$

wherein $A^1$ and $A^2$ are as defined above, and $X^8$ and $X^9$ are the same or different and each is a halogen atom, to a dehydrohalogenation reaction in the presence of a catalyst in the gas phase to produce a halogenated alkene compound represented by formula (2B):

$$CX^3A^1=CHA^2 \quad (2B)$$

wherein $A^1$, $A^2$, and $X^8$ are as defined above;

(IIB) after step (IB), removing hydrogen halide; and (IIIB) after step (IIB), subjecting the obtained halogenated alkene compound represented by formula (2B):

$$CX^8A^1=CHA^2 \quad (2B)$$

wherein $A^1$, $A^2$, and $X^3$ are as defined above, to a dehydrohalogenation reaction in the presence of a catalyst in the gas phase to produce the fluorinated alkyne compound represented by formula (3B):

$$CA^1\equiv CA^2 \quad (3B)$$

wherein $A^1$ and $A^2$ are as defined above.

(2-3-1) Step (IB)

In the method for producing a fluorinated butyne compound of the present disclosure, the explanation in the "2-1: Method for Producing Halogenated Alkene Compound from Halogenated Alkane Compound" section above can be applied to step (IB) as it is.

(2-3-2) Step (IIB)

The method for producing a fluorinated alkyne compound of the present disclosure comprises subjecting a halogenated alkane compound represented by formula (1B) to a dehydrohalogenation reaction to produce a halogenated alkene compound represented by formula (2B) (step (IB)), and then removing hydrogen halide from the mixture containing the halogenated alkene compound and hydrogen halide (step (IIB)).

In the method for producing a fluorinated alkyne compound of the present disclosure, after step (IB), the hydrogen halide generated by the dehydrohalogenation reaction in step (IB) is separated and/or removed, followed by the production of a fluorinated alkyne compound in next step (IIIB), whereby a fluorinated alkyne compound, which is a target compound, can be produced by a dehydrohalogenation reaction at a high conversion rate (yield) and high selectivity.

For the method for removing hydrogen halide from the mixture containing the halogenated alkene compound and hydrogen halide obtained in step (IB), the explanation in the "(1-3-2) Step (IIA)" section in the "Method for Producing Halogenated Butyne Compound from Halogenated Butane Compound via Halogenated Butene Compound" section above can be applied as it is, except that it is read as separating hydrogen halide instead of separating hydrogen fluoride.

(2-3-3) Step (IIIB)

In the method for producing a fluorinated alkyne compound of the present disclosure, the explanation in the "2-2: Method for Producing Fluorinated Alkyne Compound from Halogenated Alkene Compound" section above can be applied to step (IIIB) as it is.

(2-3-4) Examples of Dehydrohalogenation Reaction

In the step of performing a dehydrohalogenation reaction in the present disclosure, the reaction can be carried out in a batch process or a flow process in which the raw material compound (halogenated alkane compound) is continuously fed into the reactor and the target compound (halogenated alkene compound) is continuously withdrawn from the reactor in step (IB). Then, hydrogen halide is removed from the mixture containing the halogenated alkene compound and hydrogen halide (step (IIB)). Step (IIIB) can be carried out in a batch process or a flow process in which the raw material compound (halogenated alkene compound) is continuously fed into the reactor and the target compound (fluorinated alkyne compound) is continuously withdrawn from the reactor. In each step, the target compound (halogenated alkene compound or fluorinated alkyne compound) does not remain in the reactor, and the dehydrohalogenation reaction can further proceed; thus, it is preferable to carry out the reaction in a flow process.

In the step of performing a dehydrohalogenation reaction in the present disclosure, the reaction is preferably carried out in the gas phase, particularly by a gas-phase continuous flow process using a fixed bed reactor. When a gas-phase continuous flow process is used, the device, operation, etc. can be simplified, and it is economically advantageous.

In the step of performing a dehydrohalogenation reaction in the present disclosure, the atmosphere when performing the reaction is preferably an inert gas atmosphere, from the viewpoint of suppressing the deterioration of the catalyst (activated carbon, metal catalyst, etc.). In the present disclosure, the inert gas is preferably at least one member selected from the group consisting of nitrogen, helium, argon, and carbon dioxide. Among these inert gases, nitrogen is more preferable from the viewpoint of cost reduction. The concentration of the inert gas is preferably 0 to 50 mol % of the gas component introduced into the reactor.

In the step of performing a dehydrohalogenation reaction in the present disclosure, after the reaction is completed, as described above, purification can be optionally performed according to a conventional method, thereby obtaining the target compound (halogenated alkene compound or fluorinated alkyne compound).

3. Composition

A halogenated butene compound, a halogenated butyne compound, a halogenated alkene compound, or a fluorinated alkyne compound can be obtained as described above; however, these compounds may be obtained in the form of compositions comprising the respective target compounds.

3-1: Composition Comprising Halogenated Butene Compound or Halogenated Alkene Compound According to the production method of the present disclosure, for example, when the method described in the "1-1: Method for Producing Halogenated Butene Compound from Halogenated Butane Compound" section above is applied, for example, the halogenated butene compound represented by formula (2A) may be obtained as a composition comprising both E- and Z-isomers. Further, this composition may comprise a halogenated butyne compound represented by formula (3A):

$$CX^1X^2X^3C{\equiv}CCX^5X^6X^7 \quad (3A)$$

wherein $X^1$, $X^2$, $X^3$, $X^5$, $X^6$, and $X^7$ are as defined above, and a halogenated butadiene compound represented by formula (4):

$$CX^1X^2{=}CX^4CF{=}CX^5X^6 \quad (4)$$

wherein $X^1$, $X^2$, $X^4$, $X^5$, and $X^6$ are as defined above.

In formulas (2A), (3A), and (4), examples of the halogen atom represented by $X^1$, $X^2$, $X^3$, $X^4$, $X^5$, $X^6$, and $X^7$ include a fluorine atom, a chlorine atom, a bromine atom, and an iodine atom; preferably a fluorine atom and a chlorine atom; and more preferably a fluorine atom.

When the total amount of the composition of the present disclosure is taken as 100 mol %, the content of the halogenated butene compound represented by formula (2A) is preferably 80.00 to 99.99 mol %, more preferably 90.00 to 99.98 mol %, and even more preferably 92.00 to 99.97 mol %. Further, the content of the halogenated butyne compound represented by formula (3A) is preferably 0.00 to 3.00 mol %, and more preferably 0.01 to 2.00 mol %, but can be 1.00 to 10.00 mol % (particularly 2.00 to 8.00 mol %) depending on the synthesis conditions. Moreover, the content of the halogenated butadiene compound represented by formula (4) is preferably 0.00 to 0.50 mol %, and more preferably 0.01 to 0.30 mol %. When the halogenated butene compound represented by formula (2A) contains both E- and Z-isomers, the content mentioned above refers to the total amount thereof.

According to the production method of the present disclosure, as the halogenated butene compound represented by formula (2A), the E-isomer can be selectively synthesized. Therefore, the content of the (E)-halogenated butene compound is preferably 85.00 to 99.98 mol % (particularly 86.00 to 99.00 mol %), and the content of the (Z)-halogenated butene compound is preferably 0.01 to 15.00 mol % (particularly 1.00 to 14.00 mol %).

According to the production method of the present disclosure, even when being obtained as a halogenated butene composition, the halogenated butene compound represented by formula (2A) can be obtained at a high reaction conversion rate, and a high yield and a high selectivity, as described above. Therefore, it is possible to reduce components other than the halogenated butene compound represented by formula (2A) in the halogenated butene composition, which can reduce the purification work to obtain the halogenated butene compound represented by formula (2A).

In contrast, when the method described in the "2-1: Method for Producing Halogenated Alkene Compound from Halogenated Alkane Compound" section is applied, for example, a composition comprising the halogenated alkene compound represented by formula (2B) and at least one additional compound comprising at least one hydrofluorocarbon (HFC) compound, except for the halogenated alkene compound represented by formula (2B), can be generated.

The additional compound is preferably at least one member selected from the group consisting of hexafluorobutene, hexafluorobutane, and octafluorobutane.

Specifically, in the method for producing a halogenated alkene compound from a halogenated alkane compound of the present disclosure, when 2-chloro-1,1,1,4,4,4-hexafluoro-2-butene (1326mxz) is obtained as a target product, (Z)-1,1,1,4,4,4-hexafluorobut-2-ene (HFO-1336mzz (Z)) can be generated.

In the composition comprising the halogenated alkene compound represented by formula (2B) of the present disclosure, when the total amount of the composition is taken as 100 mol %, the content of the halogenated alkene compound represented by formula (2B) is preferably 80 mol % or more, and the content of the additional compound is preferably 20 mol % or less. In the composition comprising the halogenated alkene compound represented by formula (2B) of the present disclosure, when the total amount of the composition is taken as 100 mol %, the content of the halogenated alkene compound represented by formula (2B) is preferably 85 mol % or more, more preferably 90 mol % or more, and even more preferably 95 mol % or more. In the composition comprising the halogenated alkene compound represented by formula (2B) of the present disclosure, when the total amount of the composition is taken as 100 mol %, the content of the halogenated alkene compound represented by formula (2B) is preferably 80 to 99.9 mol %, more preferably 85 to 99.9 mol %, even more preferably 90 to 99.9 mol %, and particularly preferably 95 to 99.9 mol %.

3-2: Composition Comprising Halogenated Butyne Compound or Fluorinated Alkyne Compound According to the production method of the present disclosure, for example, when the method described in the "2-2: Method for Producing Fluorinated Alkyne Compound from Halogenated Alkene Compound" section above is applied, for example, a composition comprising the fluorinated alkyne compound represented by formula (3B) and at least one additional compound comprising at least one hydrofluorocarbon (HFC) compound, except for the fluorinated alkyne compound represented by formula (3B), can be generated. When the method describe in the "1-2: Method for Producing Halogenated Butyne Compound from Halogenated Butene Compound" section is applied, a composition comprising the halogenated butyne compound represented by formula (3A) and at least one additional compound comprising a hydrofluorocarbon (HFC) compound, except for the halogenated butyne compound represented by formula (3A), can be generated.

The additional compound is preferably at least one member selected from the group consisting of trifluoromethane, difluoromethane, tetrafluoromethane, and monofluoromethane.

In the method for producing a halogenated butyne compound from a halogenated butene compound, and the method for producing a fluorinated alkyne compound from a halogenated alkene compound of the present disclosure, when 1,1,1,4,4,4-hexafluoro-2-butyne (PF2B) is obtained as a target product, trifluoromethane (HFC-23, R23) can be generated.

In the composition comprising a halogenated butyne compound or fluorinated alkyne compound in the present disclosure, when the total amount of the composition is taken as 100 mol %, the content of the halogenated butyne compound or fluorinated alkyne compound is preferably 80 mol % or more, and the content of the additional compound is preferably 20 mol % or less. In the composition comprising a halogenated butyne compound or fluorinated alkyne compound, when the total amount of the composition is taken as 100 mol %, the content of the halogenated butyne compound or fluorinated alkyne compound is preferably 85 mol % or more, more preferably 90 mol % or more, and even more preferably 95 mol % or more. In the composition comprising a halogenated butyne compound or fluorinated alkyne compound of the present disclosure, when the total amount of the composition is taken as 100 mol %, the content of the halogenated butyne compound or fluorinated alkyne compound is preferably 80 to 99.9 mol %, more preferably 85 to 99.9 mol %, even more preferably 90 to 99.9 mol %, and particularly preferably 95 to 99.9 mol %.

3-3: Use of Composition Comprising Halogenated Butene Compound, Halogenated Butyne Compound, Halogenated Alkene Compound, or Fluorinated Alkyne Compound According to the production methods of the present disclosure, even when being obtained as a composition comprising a halogenated butene compound, a halogenated butyne compound, a halogenated alkene compound, or a fluorinated alkyne compound, the halogenated butene compound, halogenated butyne compound, halogenated alkene compound, or fluorinated alkyne compound can be obtained particularly at a high selectivity. As a result, components other than the halogenated butene compound, halogenated butyne compound, halogenated alkene compound, and fluorinated alkyne compound in the composition can be reduced. According to the production methods of the present disclosure, it is possible to reduce the purification work to obtain a halogenated butene compound, a halogenated butyne compound, a halogenated alkene compound, or a fluorinated alkyne compound.

The composition comprising a halogenated butene compound, a halogenated butyne compound, a halogenated alkene compound, or a fluorinated alkyne compound of the present disclosure can be effectively used for various applications, such as etching gases for forming cutting-edge microstructures in semiconductors, liquid crystals, etc., as well as cleaning gases, deposit gases, refrigerants, heat transfer media, and building blocks for organic synthesis, as in the case of the halogenated butene compound, halogenated butyne compound, halogenated alkene compound, or fluorinated alkyne compound alone.

The deposit gas is a gas that deposits an etching resistant polymer layer.

The building block for organic synthesis refers to a substance that can be a precursor of a compound having a highly reactive skeleton. For example, when the composition of the present disclosure is reacted with a fluorine-containing organosilicon compound, such as $CF_3Si(CH_3)_3$, it is possible to introduce a fluoroalkyl group, such as a $CF_3$ group, to convert it into a substance that can be a cleaner or a fluorine-containing pharmaceutical intermediate.

Although the embodiments are described above, various changes in form and details can be made without departing from the spirit and scope of the claims.

The present disclosure includes the following configurations.

Item 1. A method for producing a halogenated butene compound represented by formula (2A):

$$CX^1X^2X^3CX^4\!=\!CHCX^5X^6X^7 \quad (2A)$$

wherein $X^1$, $X^2$, $X^3$, $X^4$, $X^5$, $X^6$, and $X^7$ are the same or different and each is a halogen atom, the method comprising subjecting a halogenated butane compound represented by formula (1A):

$$CX^1X^2X^3CHX^4CFHCX^5X^6X^7 \quad (1A)$$

wherein $X^1$, $X^2$, $X^3$, $X^4$, $X^5$, $X^6$, and $X^7$ are as defined above, to a dehydrofluorination reaction.

Item 2. A method for producing a halogenated butyne compound represented by formula (3A):

$$CX^1X^2X^3C\!\equiv\!CCX^5X^6X^7 \quad (3A)$$

wherein $X^1$, $X^2$, $X^3$, $X^5$, $X^6$, and $X^7$ are the same or different and each is a halogen atom, the method comprising subjecting a halogenated butene compound represented by formula (2A):

$$CX^1X^2X^3CX^4\!=\!CHCX^5X^6X^7 \quad (2A)$$

wherein $X^1$, $X^2$, $X^3$, $X^5$, $X^6$, and $X^7$ are as defined above, and $X^4$ is a halogen atom, to a dehydrohalogenation reaction.

Item 3. A method for producing a halogenated butyne compound represented by formula (3A):

$$CX^1X^2X^3C\!\equiv\!CCX^5X^6X^7 \quad (3A)$$

wherein $X^1$, $X^2$, $X^3$, $X^5$, $X^6$, and $X^7$ are the same or different and each is a halogen atom, the method comprising:

(IA) subjecting a halogenated butane compound represented by formula (1A):

$$CX^1X^2X^3CHX^4CFHCX^5X^6X^7 \quad (1A)$$

wherein $X^1$, $X^2$, $X^3$, $X^5$, $X^6$, and $X^7$ are as defined above, and $X^4$ is a halogen atom, to a dehydrofluorination reaction to produce a halogenated butene compound represented by formula (2A):

$$CX^1X^2X^3CX^4\!=\!CHCX^5X^6X^7 \quad (2A)$$

wherein $X^1$, $X^2$, $X^3$, $X^4$, $X^5$, $X^6$, and $X^7$ are as defined above;

(IIA) after step (IA), removing hydrogen fluoride; and (IIIA) after step (IIA), subjecting the obtained halogenated butene compound represented by formula (2A):

$$CX^1X^2X^3CX^4\!=\!CHCX^5X^6X^7 \quad (2A)$$

wherein $X^1$, $X^2$, $X^3$, $X^4$, $X^5$, $X^6$, and $X^7$ are as defined above, to a dehydrohalogenation reaction to produce the halogenated butyne compound represented by formula (3A):

$$CX^1X^2X^3C\!\equiv\!CCX^5X^6X^7 \quad (3A)$$

wherein $X^1$, $X^2$, $X^3$, $X^5$, $X^6$, and $X^7$ are as defined above.

Item 4. The production method according to any one of Items 1 to 3, wherein the step of the dehydrofluorination reaction and/or the dehydrohalogenation reaction is performed in the presence of a catalyst and/or a base.

Item 5. The production method according to any one of Items 1 to 4, wherein the step of the dehydrofluorination reaction and/or the dehydrohalogenation reaction is performed in a liquid phase.

Item 6. The production method according to Item 5, wherein the step of the dehydrofluorination reaction and/or the dehydrohalogenation reaction is performed in a closed reaction process.

Item 7. The production method according to any one of Items 1 to 4, wherein the step of the dehydrofluorination reaction and/or the dehydrohalogenation reaction is performed in a gas phase.

Item 8. The production method according to Item 7, wherein the step of the dehydrofluorination reaction and/or the dehydrohalogenation reaction is performed in the presence of at least one catalyst selected from the group consisting of an activated carbon catalyst, a chromium oxide catalyst, a zeolite catalyst, and a silica alumina catalyst.

Item 9. A method for producing a halogenated alkene compound represented by formula (2B):

$$CX^8A^1\!=\!CHA^2 \quad (2B)$$

wherein $A^1$ and $A^2$ are the same or different and each is a fluorine atom or a perfluoroalkyl group, and $X^8$ is a halogen atom, the method comprising subjecting a halogenated alkane compound represented by formula (1B):

$$CHX^8A^1CHX^9A^2 \quad (1B)$$

wherein $A^1$ and $A^2$ are as defined above, and $X^8$ and $X^9$ are the same or different and each is a halogen atom, to a dehydrohalogenation reaction in the presence of a catalyst in a gas phase.

Item 10. A method for producing a fluorinated alkyne compound represented by formula (3B):

$$CA^1{\equiv}CA^2 \quad (3B)$$

wherein $A^1$ and $A^2$ are the same or different and each is a fluorine atom or a perfluoroalkyl group, the method comprising subjecting a halogenated alkene compound represented by formula (2B):

$$CX^8A^1{=}CHA^2 \quad (2B)$$

wherein $A^1$ and $A^2$ are as defined above, and $X^8$ is a halogen atom, to a dehydrohalogenation reaction in the presence of a catalyst.

Item 11. The production method according to Item 10, wherein the step of the dehydrohalogenation reaction is performed in a gas phase.

Item 12. A method for producing a fluorinated alkyne compound represented by formula (3B):

$$CA^1{\equiv}CA^2 \quad (3B)$$

wherein $A^1$ and $A^2$ are the same or different and each is a fluorine atom or a perfluoroalkyl group, the method comprising:

(IB) subjecting a halogenated alkane compound represented by formula (1B):

$$CHX^8A^1CHX^9A^2 \quad (1B)$$

wherein $A^1$ and $A^2$ are as defined above, and $X^8$ and $X^9$ are the same or different and each is a halogen atom, to a dehydrohalogenation reaction in the presence of a catalyst in a gas phase to produce a halogenated alkene compound represented by formula (2B):

$$CX^8A^1{=}CHA^2 \quad (2B)$$

wherein $A^1$, $A^2$, and $X^8$ are as defined above; (IIB) after step (IB), removing hydrogen halide; and (IIIB) after step (IIB), subjecting the obtained halogenated alkene compound represented by formula (2B):

$$CX^8A^1{=}CHA^2 \quad (2B)$$

wherein $A^1$, $A^2$, and $X^3$ are as defined above, to a dehydrohalogenation reaction in the presence of a catalyst in a gas phase to produce the fluorinated alkyne compound represented by formula (3B):

$$CA^1{\equiv}CA^2 \quad (3B)$$

wherein $A^1$ and $A^2$ are as defined above.

Item 13. The production method according to any one of Items 1 to 12, wherein the step of the dehydrofluorination reaction and/or the dehydrohalogenation reaction is performed by a gas-phase continuous flow process.

Item 14. The production method according to any one of Items 1 to 13, wherein the step of the dehydrofluorination reaction and/or the dehydrohalogenation reaction is performed in the presence of a cyclic halogen carbide compound in which all hydrogen atoms bonded to carbon atoms in a hydrocarbon compound are replaced by halogen atoms.

Item 15. A composition comprising a halogenated butene compound represented by formula (1A):

$$CX^1X^2X^3CX^4{=}CHCX^5X^6X^7 \quad (1A)$$

wherein $X^1$, $X^2$, $X^3$, $X^4$, $X^5$, $X^6$, and $X^7$ are the same or different and each is a halogen atom, the halogenated butene compound represented by formula (1A) being contained in an amount of 80.00 to 99.99 mol % based on the total amount of the composition, which is taken as 100 mol %.

Item 16. The composition according to Item 15, comprising, as the halogenated butene compound represented by formula (1A), an (E)-halogenated butene compound in an amount of 85.00 to 99.98 mol % based on the total amount of the composition, which is taken as 100 mol %.

Item 17. A composition comprising:

a halogenated alkene compound represented by formula (2B):

$$CX^8A^1{=}CHA^2 \quad (2B)$$

wherein $A^1$ and $A^2$ are the same or different and each is a fluorine atom or a perfluoroalkyl group, and $X^8$ is a halogen atom; and at least one hydrofluorocarbon (HFC) compound, except for the halogenated alkene compound represented by formula (2B).

Item 18. The composition according to Item 17, wherein the halogenated alkene compound represented by formula (2B) is contained in an amount of 80 mol % or more, and the hydrofluorocarbon (HFC) compound is contained in an amount of 20 mol % or less, based on the total amount of the composition, which is taken as 100 mol %.

Item 19. The composition according to Item 17 or 18, wherein the hydrofluorocarbon (HFC) compound is at least one member selected from the group consisting of hexafluorobutene, hexafluorobutane, and octafluorobutane.

Item 20. A composition comprising:

a fluorinated alkyne compound represented by formula (3B):

$$CA^1{\equiv}CA^2 \quad (3B)$$

wherein $A^1$ and $A^2$ are the same or different and each is a fluorine atom or a perfluoroalkyl group; and at least one hydrofluorocarbon (HFC) compound, except for the fluorinated alkyne compound represented by formula (3B).

Item 21. A composition comprising:

a halogenated butyne compound represented by formula (3A):

$$CX^1X^2X^3C{\equiv}CCX^5X^6X^7 \quad (3A)$$

wherein $X^1$, $X^2$, $X^3$, $X^5$, $X^6$, and $X^7$ are the same or different and each is a halogen atom; and at least one hydrofluorocarbon (HFC) compound, except for the halogenated butyne compound represented by formula (3A).

Item 22. The composition according to Item 20 or 21, wherein the fluorinated alkyne compound represented by formula (3B) or the halogenated butyne compound represented by formula (3A) is contained in an amount of 80 mol % or more, and the hydrofluorocarbon (HFC) compound is contained in an amount of 20 mol % or less, based on the total amount of the composition, which is taken as 100 mol %.

Item 23. The composition according to any one of Items 20 to 22, wherein the hydrofluorocarbon (HFC) compound is at least one member selected from the group consisting of trifluoromethane, difluoromethane, tetrafluoromethane, and monofluoromethane.

Item 24. The composition according to any one of Items 15 to 23, which is used as a cleaning gas, an etching gas, a refrigerant, a heat transfer medium, or a building block for organic synthesis.

EXAMPLES

The features of the present disclosure are clarified below while showing Examples. The present disclosure is not limited to these Examples.

In the methods for producing a halogenated butene compound of Examples 1 to 7, the raw material compound was a halogenated butane compound represented by formula (1A) wherein $X^1$, $X^2$, $X^3$, $X^4$, $X^5$, $X^6$, and $X^7$ are fluorine atoms, and a halogenated butene compound was obtained by a dehydrofluorination reaction according to the following reaction formula:

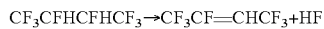
$CF_3CFHCFHCF_3 \rightarrow CF_3CF=CHCF_3 + HF$

In the methods for producing a halogenated alkene compound and a fluorinated butyne compound of Example 8, the raw material compound was a halogenated alkane compound represented by formula (1B) wherein $X^8$ and $X^9$ are chlorine atoms, and $A^1$ and $A^2$ are trifluoromethyl groups, and a halogenated alkene compound and a fluorinated butyne compound were obtained by a dehydrochlorination reaction according to the following reaction formulas:

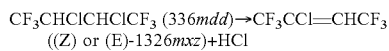
$CF_3CHClCHClCF_3$ (336mdd) $\rightarrow CF_3CCl=CHCF_3$ ((Z) or (E)-1326mxz)+HCl

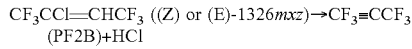
$CF_3CCl=CHCF_3$ ((Z) or (E)-1326mxz) $\rightarrow CF_3C\equiv CCF_3$ (PF2B)+HCl In the methods for producing a halogenated alkene compound and a fluorinated butyne compound of Examples 9 to 20, the raw material compound was a halogenated alkane compound represented by formula (1B) wherein $X^8$ and $X^9$ are fluorine atoms, and $A^1$ and $A^2$ are trifluoromethyl groups, and a halogenated alkene compound and a fluorinated butyne compound were obtained by a dehydrofluorination reaction according to the following reaction formulas:

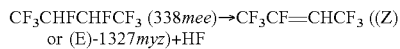
$CF_3CHFCHFCF_3$ (338mee) $\rightarrow CF_3CF=CHCF_3$ ((Z) or (E)-1327myz)+HF

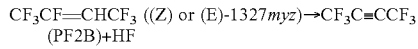
$CF_3CF=CHCF_3$ ((Z) or (E)-1327myz) $\rightarrow CF_3C\equiv CCF_3$ (PF2B)+HF Examples 1 to 3: Liquid-Phase Reaction An autoclave (200 cc) was used as a reaction system.

Due to the use of an autoclave as a reaction system, this reaction system refers to (1) a closed reaction process in the presence of a base, or (2) a pressure-increased reaction process performed in the presence of a base at a reaction temperature of 10° C. or higher at a reaction pressure of 0 kPa or more. When pressurizing in this way, sealing is involved.

To the autoclave, 7.0 g of 50 mass % aqueous solution of KOH or 50 mass % dibutyl ether ($Bu_2O$) solution of potassium tert-butoxide (t-BuOK) was added as a reaction solution. If necessary, 0.28 g of methyltrioctylammonium chloride (trademark: Aliquat 336) was added as a catalyst. Further, 8.0 g of the raw material compound ($CF_3CFHCFHCF_3$) was added. After the lid was closed to create a closed system, nitrogen was fed and pressed. The pressure at that time was 20 kPa. Then, stirring was performed at room temperature (25° C.) to promote the reaction. After the dehydrofluorination reaction was started, sampling was performed as appropriate. The reaction was stopped when there was no change in the composition within the reaction system. The pressure at the end of the reaction was 80 kPa.

After stirring was stopped, the resultant was cooled to 0° C. Then, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH"). From the results of mass spectrometry and structural analysis, it was confirmed that $CF_3CF=CHCF_3$ was produced as a target compound. The results are shown in Table 1.

Examples 4 to 6: Gas-Phase Reaction (Activated Carbon)

A SUS pipe (outer diameter: ½ inch) as a reaction tube was filled with, as a catalyst, 10 g of activated carbon catalyst (produced by Osaka Gas Chemicals Co., Ltd.; specific surface area: 1200 $m^2/g$). After drying at 200° C. for 2 hours in a nitrogen atmosphere, $CF_3CFHCFHCF_3$ (raw material compound) was allowed to flow through the reaction tube at normal pressure so that the contact time (W/F) of $CF_3CFHCFHCF_3$ (raw material compound) and the activated carbon catalyst was 15 g·sec/cc, 30 g·sec/cc, or 47 g·sec/cc.

The reaction was allowed to proceed by a gas-phase continuous flow process.

The reaction tube was heated at 450° C. to start the dehydrofluorination reaction.

One hour after the start of the dehydrofluorination reaction, the distillate that passed through the abatement column was collected.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH"). From the results of mass spectrometry and structural analysis, it was confirmed that $CF_3CF=CHCF_3$ was produced as a target compound. The results are shown in Table 1.

Example 7: Gas-Phase Reaction (Chromium Oxide Catalyst)

The reaction was allowed to proceed in the same manner as in Examples 4 to 6, except that a chromium oxide catalyst ($Cr_2O_3$) was used as the catalyst, the reaction temperature was 350° C., and the contact time (W/F) of $CF_3CFHCFHCF_3$ (raw material compound) and the chromium oxide catalyst was 47 g·sec/cc. From the results of mass spectrometry and structural analysis, it was confirmed that $CF_3CF=CHCF_3$ was produced as a target compound. The results are shown in Table 1.

TABLE 1

| | Example | | | | | | |
|---|---|---|---|---|---|---|---|
| | 1 | 2 | 3 | 4 | 5 | 6 | 7 |
| Reaction | Liquid phase | Liquid phase | Liquid phase | Gas phase | Gas phase | Gas phase | Gas phase |
| Solvent | Water | Bu$_2$O | Water | — | — | — | — |
| Base | KOH | t-uOK | KOH | — | — | — | — |
| Catalyst | Aliquat 336 | — | — | Activated carbon | Activated carbon | Activated carbon | Cr$_2$O$_3$ |
| Temperature (° C.) | 25 | 60 | 25 | 450 | 450 | 450 | 350 |
| W/F (g · sec/cc) | — | — | — | 47 | 30 | 15 | 47 |
| Reaction time (h) | 0.5 | 2 | 5 | 1 | 1 | 1 | 1 |
| Conversion rate (mol %) | 95.2 | 89.2 | 93.4 | 99.1 | 99.0 | 98.0 | 80.1 |
| Setectivtty (mol %) | | | | | | | |
| CF$_3$CF=CHCF$_3$ | 99.48 | 96.85 | 99.17 | 97.6 | 97.0 | 984 | 94.1 |
| E-isomer | 98.58 | 96.03 | 97.17 | 86.3 | 86.9 | 89.1 | 87.2 |
| Z-isomer | 0.90 | 0.82 | 2.00 | 11.3 | 10.1 | 9.3 | 6.9 |
| CF$_3$C≡CCF$_3$ | 0.220 | 2.54 | 0.11 | 0.72 | 0.71 | 0.69 | 0.6 |
| CF$_2$=CFCF=CF$_2$ | 0.001 | 0.02 | 0.001 | 0.10 | 0.10 | 0.10 | 0.002 |
| Others | 0.30 | 0.81 | 0.73 | 1.52 | 2.09 | 0.71 | 5.30 |
| Total | 100 | 100 | 100 | 100 | 100 | 100 | 100 |

Example 8 (Dehydrochlorination)

336mdd (CF$_3$CHClCHClCF$_3$)→1326mxz (CF$_3$CCl=CHCF$_3$)→PF2B (CF$_3$C≡CCF$_3$)

(1) 336mdd (CF$_3$CHClCHClCF$_3$)→1326 mxz (CF$_3$CCl=CHCF$_3$)

A SUS pipe (outer diameter: ½ inch) was used as a reaction tube and filled with, as a catalyst, 10 g of activated carbon catalyst (specific surface area: 1200 m$^2$/g). After drying at 200° C. for 2 hours in a nitrogen atmosphere, CF$_3$CHClCHClCF$_3$ (raw material compound) was allowed to flow through the reactor at normal pressure so that the contact time (W/F$_0$) of CF$_3$CHClCHClCF$_3$ (raw material compound) and the activated carbon catalyst was 5 g·sec/cc or 25 g·sec/cc.

The reaction was allowed to proceed by a gas-phase continuous flow process.

The reactor was heated at 300° C. or 400° C. to start dehydrochlorination.

(2) Removal of Hydrogen Chloride

One hour after the start of dehydrochlorination, the distillate that passed through the abatement column was collected.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH").

From the results of mass spectrometry and structural analysis, it was confirmed that a halogenated alkene compound (1326mxz: CF$_3$CCl=CHCF$_3$) was produced as a target compound.

Further, in the method for producing a halogenated alkene compound from a halogenated alkane compound, (Z)-1,1,1,4,4,4-hexafluorobut-2-ene (HFO-1336mzz (Z)) was produced as a target product, in addition to 1326mxz (CF$_3$CCl=CHCF$_3$).

TABLE 2

Table 2: 336mdd (CF$_3$CHClCHClCF$_3$) → 1326mxz (CF$_3$CC=CHCN$_3$)

| | Reacton temperature (° C.) | Contact time W/F$_0$ (g · sec/cc) | Conversion rate from raw material compound 336mdd (mol %) | Selectivity (mol %) | | | | | | |
|---|---|---|---|---|---|---|---|---|---|---|
| | | | | Target compound 1326mxz | R23 | PF2B | 1327myz | Z1336mzz | 1316mxx | Others |
| Example 8-1 | 300 | 5 | 94.08 | 95.89 | 0.00 | 0.00 | 0.00 | 2.71 | 0.73 | 0.67 |
| Example 8-2 | 300 | 25 | 93.36 | 96.02 | 0.00 | 0.00 | 0.00 | 3.18 | 0.42 | 0.38 |
| Example 8-3 | 400 | 5 | 97.21 | 89.90 | 0.04 | 0.15 | 0.06 | 4.58 | 2.27 | 2.49 |
| Example 8-4 | 400 | 25 | 91.85 | 90.26 | 0.04 | 0.09 | 0.31 | 5.59 | 1.92 | 1.18 |

336mdd: CF$_3$CHClCHClCF$_3$
1326mxz: CF$_3$CC=CHCF$_3$
R23: CHF$_3$
PF2B: CF$_3$C≡CCF$_3$
1327myz: CF$_3$CF=CHCF$_3$
Z1336mzz: CF$_3$CH=CHCF$_3$
1316mxx: CF$_3$CCl=CClCF$_3$ (3) 1326mxz (CF$_3$CCl=CHCF$_3$)→PF2B (CF$_3$C≡CCF$_3$)

A SUS pipe (outer diameter: ½ inch) was used as a reaction tube and filled with, as a catalyst, 10 g of activated carbon catalyst (specific surface area: 1200 m$^2$/g).

le;2qIn this operation, the reaction was carried out by returning a reactive gas containing the halogenated alkene compound produced in the above manner to the reactor (first reactor)

again, or by allowing it to flow in the next reactor (second reactor) filled with the activated carbon catalyst.

At that time, the hydrogen chloride concentration of the reactive gas containing the halogenated alkene compound was 50 mol %. The reactive gas from the first reactor was subjected to rectification, alkali treatment, Secard treatment, alumina treatment, or the like to adjust the hydrogen chloride concentration to 20 mol %, 3 mol %, or 0.1 mol %.

After drying at 200° C. for 2 hours in a nitrogen atmosphere, $CF_3CCl=CHCF_3$ (raw material compound) was allowed to flow through the reactor at normal pressure so that the contact time ($W/F_0$) of $CF_3CCl=CHCF_3$ (raw material compound) and the activated carbon catalyst was 0.5 g·sec/cc, 20 g·sec/cc, or 43 g·sec/cc.

The reaction was allowed to proceed by a gas-phase continuous flow process.

The reactor was heated at 400° C. to start dehydrochlorination.

One hour after the start of dehydrochlorination, the distillate that passed through the abatement column was collected.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH").

From the results of mass spectrometry and structural analysis, it was confirmed that a fluorinated alkyne compound (PF2B ($CF_3C{\equiv}CCF_3$)) was produced as a target compound.

Further, in the method for producing a fluorinated alkyne compound from a halogenated alkene compound, trifluoromethane (HFC-23, R23) was produced as a target product, in addition to PF2B.

TABLE 3

Table 3: 1326mxz ($CF_3CCl=CHCF_3$) → PF2B ($CF_3C{\equiv}CCF_3$)

| | Reacton temperature (° C.) | Contact time $W/F_0$ (g · sec/cc) | Conversion rate from raw material compound 1326mx (mol %) | Selectivity (mol %) | | | |
|---|---|---|---|---|---|---|---|
| | | | | Target compound PF2B | 1327myz | R23 | others |
| Hydrochloric acid concentration: 0.1 mol % | | | | | | | |
| Example 8-5 | 400 | 43 | 14.32 | 2.80 | 81.09 | 0.34 | 15.77 |
| Example 8-6 | 400 | 20 | 14.21 | 10.43 | 70.64 | 0.34 | 18.59 |
| Example 8-7 | 400 | 0.5 | 13.20 | 96.50 | 4.32 | 0.21 | 3.29 |
| Hydrochloric acid concentration: 3 mol % | | | | | | | |
| Example 8-8 | 400 | 43 | 14.32 | 2.10 | 83.09 | 0.34 | 14.81 |
| Example 8-9 | 400 | 20 | 14.21 | 9.43 | 79.54 | 0.34 | 11.03 |
| Example 8-10 | 400 | 0.5 | 13.20 | 85.50 | 9.44 | 0.21 | 5.06 |
| Hydrochloric acid concentration: 20 mol % | | | | | | | |
| Example 8-11 | 400 | 43 | 5.33 | 0.09 | 31.32 | 0.01 | 69.58 |
| Example 8-12 | 400 | 20 | 6.43 | 5.12 | 10.11 | 0.20 | 84.57 |
| Example 8-13 | 400 | 0.5 | 6.21 | 5.17 | 4.04 | 0.03 | 90.76 |
| Hydrochloric acid concentration: 50 mol % | | | | | | | |
| Example 8-14 | 400 | 43 | 1.25 | 0.09 | 0.32 | 0.01 | 99.58 |
| Example 8-15 | 400 | 20 | 0.89 | 0.12 | 0.11 | 0.20 | 99.57 |
| Example 8-16 | 400 | 0.5 | 0.88 | 0.17 | 0.04 | 0.03 | 99.76 |

1326mxz: $CF_3CCl=CHCF_3$

PF2B: $CF_3C{\equiv}CCF_3$

R23: $CHF_3$

1327myz: $CF_3CF=CHCF_3$

Example 9 (Dehydrofluorination)

338mee (CF$_3$CHFCHFCF$_3$)→1327myz (CF$_3$CF=CHCF$_3$)→PF2B (CF$_3$C≡CCF$_3$)

(1) 338mee (CF$_3$CHFCHF$_3$)→1327myz (CF$_3$CF=CHCF$_3$)

A SUS pipe (outer diameter: ½ inch) was used as a reaction tube and filled with, as a catalyst, 10 g of activated carbon catalyst (specific surface area: 1200 m$^2$/g).

After drying at 200° C. for 2 hours in a nitrogen atmosphere, CF$_3$CHFCHFCF$_3$ (raw material compound) was allowed to flow through the reactor at normal pressure so that the contact time (W/F$_0$) of CF$_3$CHFCHFCF$_3$ (raw material compound) and the activated carbon catalyst was 5 g·sec/cc or 25 g·sec/cc.

The reaction was allowed to proceed by a gas-phase continuous flow process.

The reactor was heated at 100° C., 200° C., 300° C., or 400° C. to start dehydrofluorination.

(2) Removal of Hydrogen Fluoride

One hour after the start of dehydrofluorination, the distillate that passed through the abatement column was collected.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH").

From the results of mass spectrometry and structural analysis, it was confirmed that a halogenated alkene compound (1327myz: CF$_3$=CHCF$_3$) was produced as a target compound.

(3) 1327myz (CF$_3$CF=CHCF$_3$)→PF2B (CF$_3$C≡CCF$_3$)

A SUS pipe (outer diameter: ½ inch) was used as a reaction tube and filled with, as a catalyst, 10 g of activated carbon catalyst (specific surface area: 1200 m$^2$/g).

In this operation, the reaction was carried out by returning a reactive gas containing the halogenated alkene compound produced in the above manner to the reactor (first reactor) again, or by allowing it to flow in the next reactor (second reactor) filled with the activated carbon catalyst.

At that time, the hydrogen chloride concentration of the reactive gas containing the halogenated alkene compound was 50 mol %. The reactive gas from the first reactor was subjected to rectification, alkali treatment, Secard treatment, alumina treatment, or the like to adjust the hydrogen chloride concentration to 20 mol %, 3 mol %, or 0.1 mol %.

After drying at 200° C. for 2 hours in a nitrogen atmosphere, CF$_3$CF=CHCF$_3$ (raw material compound) was allowed to flow through the reactor at normal pressure so that the contact time (W/F$_0$) of CF$_3$CCl=CHCF$_3$ (raw material compound) and the activated carbon catalyst was 0.5 g·sec/cc, 20 g·sec/cc, or 43 g·sec/cc.

The reaction was allowed to proceed by a gas-phase continuous flow process.

The reactor was heated at 400° C. to start dehydrofluorination.

One hour after the start of dehydrofluorination, the distillate that passed through the abatement column was collected.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH").

From the results of mass spectrometry and structural analysis, it was confirmed that a fluorinated alkyne compound (PF2B (CF$_3$C≡CCF$_3$)) was produced as a target compound.

Further, in the method for producing a fluorinated alkyne compound from a halogenated alkene compound, trifluoromethane (HET-23, R23) was produced as a target product, in addition to PF2B.

TABLE 4

Table 4: 1327myz (CF$_3$CF=CHCF$_3$) → PF2B (CF$_3$C≡CCF$_3$)

| | Reaction temperature (° C.) | Contact time W/F$_0$ (g · sec/cc) | Conversion rate from raw material compound 1327myz (mol %) | Selectivity (mol %) Target compound PF2B | R23 | Others |
|---|---|---|---|---|---|---|
| Hydrofluoric acid concentration: 0.1 mol % | | | | | | |
| Example 9-1 | 400 | 40 | 2.4 | 77.4 | 11.2 | 11.3 |
| Example 9-2 | 400 | 10 | 13.2 | 89.5 | 1.1 | 9.4 |
| Example 9-3 | 400 | 2.8 | 27.9 | 98.8 | 0.4 | 0.7 |
| Hydrofluoric acid concentration: 3 mol % | | | | | | |
| Example 9-4 | 400 | 40 | 2.7 | 76.9 | 11.2 | 11.9 |
| Example 9-5 | 400 | 10 | 12.9 | 89.9 | 1.2 | 8.9 |
| Example 9-6 | 400 | 2.8 | 28.2 | 98.8 | 0.7 | 0.5 |
| Hydrofluoric acid concentration: 20 mol % | | | | | | |
| Example 9-7 | 400 | 40 | 0.8 | 0.09 | 0.01 | 99.9 |
| Example 9-8 | 400 | 10 | 1.2 | 1.12 | 0.19 | 98.7 |
| Example 9-9 | 400 | 2.8 | 3.3 | 2.11 | 0.03 | 97.9 |

1327myz: CF$_3$CF=CHCF$_3$
PF2B: CF$_3$C≡CCF$_3$
R23: CHF$_3$

Examples 10 to 16 (Dehydrofluorination)

338mee ($CF_3CHFCHFCF_3$)→1327myz ($CF_3CF=CHCF_3$)

A SUS pipe (outer diameter: ½ inch) was used as a reaction tube and filled with, as a catalyst, 10 g of activated carbon catalyst (specific surface area: 1200 m²/g). After drying at 200° C. for 2 hours in a nitrogen atmosphere, $CF_3CHFCHFCF_3$ (raw material compound) was allowed to flow through the reactor at normal pressure so that the contact time ($W/F_0$) of $CF_3CHFCHFCF_3$ (raw material compound) and the activated carbon catalyst was 2 to 47 g·sec/cc. Thereafter, in Examples 10 to 13, 4 mol of octafluorocyclobutane (c-$C_4F_8$; C318) was allowed to flow per mol of $CF_3CHFCHFCF_3$ (raw material compound).

The reaction was allowed to proceed by a gas-phase continuous flow process.

The reactor was heated at 400° C. to start dehydrochlorination.

One hour after the start of dehydrochlorination, the distillate that passed through the abatement column was collected.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH").

From the results of mass spectrometry and structural analysis, it was confirmed that a halogenated alkene compound (1327myz: $CF_3CF=CHCF_3$) was produced as a target compound.

Further, in the method for producing a halogenated alkene compound from a halogenated alkane compound, 1,1,1,4,4,4-hexafluorobut-2-ene (HEO-1336mzz), 1,1,1,4,4,4-hexafluoro-2-butyne (PF2B), etc. were produced as target products, in addition to 1327myz ($CF_3CF=CHCF_3$).

TABLE 5

Table 5: 338mee ($CF_3CHFCHFCF_3$) → 1327myz ($CF_3CF=CHCF_3$)

| | Reaction temperature (° C.) | Contact time $W/F_0$ (g · sec/cc) | Molar ratio C318/336mee | Conversion rate from raw material compound 336mee (mol %) | Selectivity (mol %) | | | |
|---|---|---|---|---|---|---|---|---|
| | | | | | Target compound 1327myz | PF2B | 1336mzz | Others |
| Example 10 | 400 | 15 | 4 | 93.31 | 82.60 | 1.38 | 10.88 | 5.14 |
| Example 11 | 400 | 6 | 4 | 97.54 | 94.44 | 5.02 | 0.00 | 0.53 |
| Example 12 | 400 | 3 | 4 | 93.85 | 93.01 | 5.66 | 0.00 | 1.33 |
| Example 13 | 400 | 2 | 4 | 91.45 | 90.95 | 6.05 | 0.00 | 3.00 |
| Example 14 | 400 | 47 | Without C318 | 41.22 | 94.08 | 0.12 | 0.00 | 5.80 |
| Example 15 | 400 | 20 | Without C318 | 22.21 | 94.99 | 0.14 | 0.00 | 4.87 |
| Example 16 | 400 | 10 | Without C318 | 10.22 | 97.08 | 0.09 | 0.00 | 2.83 |

336mee: $CF_3CHFCHFCF_3$

1327myz: $CF_3CF=CHCF_3$

PF2B: $CF_3C\equiv CCF_3$

1336mzz: $CF_3CH=CHCF_3$

Examples 17 to 20 (Dehydrofluorination)

1327myz ($CF_3CF=CHCF_3$)→PF2B ($CF_3C\equiv CCF_3$)

A SUS pipe (outer diameter: ½ inch) was used as a reaction tube and filled with, as a catalyst, 10 g of activated carbon catalyst (specific surface area: 1200 m$^2$/g). After drying at 200° C. for 2 hours in a nitrogen atmosphere, $CF_3CF=CHCF_3$ (raw material compound) was allowed to flow through the reactor at normal pressure so that the contact time (W/F$_0$) of $CF_3CF=CHCF_3$ (raw material compound) and the activated carbon catalyst was 2 g·sec/cc, 2.8 g·sec/cc, or 10 g·sec/cc. Thereafter, in Examples 17 to 18, 4 mol of octafluorocyclobutane (c-$C_4F_8$; C318) was allowed to flow per mol of $CF_3CF=CHCF_3$ (raw material compound).

The reaction was allowed to proceed by a gas-phase continuous flow process.

The reactor was heated at 400° C. to start dehydrochlorination.

One hour after the start of dehydrochlorination, the distillate that passed through the abatement column was collected.

After that, mass spectrometry was performed by gas chromatography/mass spectrometry (GC/MS) using a gas chromatograph (produced by Shimadzu Corporation, trade name: "GC-2014"). Structural analysis using NMR spectra was performed using NMR (produced by JEOL Ltd., trade name: "400YH").

From the results of mass spectrometry and structural analysis, it was confirmed that a fluorinated alkyne compound (PF2B: $CF_3C\equiv CCF_3$) was produced as a target compound.

Further, in the method for producing a halogenated alkene compound from a halogenated alkane compound, trifluoromethane (HFC-23, R23) was produced as a target product, in addition to PF2B ($CF_3C\equiv CCF_3$).

TABLE 6

Table 6: 1327myz ($CF_3CF=CHCF_3$) → PF2B ($CF_3C\equiv CCF_3$)

| | Reaction temperature (° C.) | Contact time W/F$_0$ (g · sec/cc) | Molar ratio C318/336mee | Conversion rate from raw material compound 1327myz (mol %) | Selectivity (mol %) | | |
|---|---|---|---|---|---|---|---|
| | | | | | Target compound PF2B | R23 | Others |
| Example 17 | 400 | 10 | 4 | 42.9 | 98.16 | 1.30 | 0.54 |
| Example 18 | 400 | 2 | 4 | 52.5 | 98.28 | 1.20 | 0.52 |
| Example 19 | 400 | 10 | Without C318 | 13.19 | 89.53 | 1.12 | 9.36 |
| Example 20 | 400 | 2.8 | Without C318 | 27.87 | 98.83 | 0.43 | 0.74 |

1327myz: $CF_3CF=CHCF_3$

PF2B: $CF_3C\equiv CCF_3$

R23: $CHF_3$

The invention claimed is:

1. A method for producing a composition containing a halogenated butene compound represented by formula (2A):

$$CX^1X^2X^3CX^4=CHCX^5X^6X^7 \quad (2A)$$

wherein $X^1$, $X^2$, $X^3$, $X^4$, $X^5$, $X^6$, and $X^7$ are the same or different and each is a halogen atom, wherein, as the halogenated butene compound represented by formula (2A), an (E)-halogenated butene compound in an amount of 85.00 to 99.98 mol % is present based on the total amount of the composition, which is taken as 100 mol %, the method comprising subjecting a halogenated butane compound represented by formula (1A):

$$CX^1X^2X^3CHX^4CFHCX^5X^6X^7 \quad (1A)$$

wherein $X^1$, $X^2$, $X^3$, $X^4$, $X^5$, $X^6$, and $X^7$ are as defined above, to a dehydrofluorination reaction in a gas phase or a liquid phase, wherein the dehydrofluorination reaction is performed in the presence of at least one catalyst selected from the group consisting of an activated carbon catalyst, a chromium oxide catalyst, and a silica alumina catalyst, when the dehydrofluorination reaction is performed in a gas phase.

2. The production method according to claim 1, wherein the step of the dehydrofluorination reaction is performed in a liquid phase.

3. The production method according to claim 2, wherein the step of the dehydrofluorination reaction is performed in the presence of a base.

4. The production method according to claim 2, wherein the step of the dehydrofluorination reaction is performed in a closed reaction process.

5. The production method according to claim 1, wherein the step of the dehydrofluorination reaction is performed in a gas phase.

6. The production method according to claim 1, wherein the step of the dehydrofluorination reaction is performed by a gas-phase continuous flow process.

7. The production method according to claim 1, wherein the step of the dehydrofluorination reaction is performed in the presence of a cyclic halogen carbide compound in which all hydrogen atoms bonded to carbon atoms in a hydrocarbon compound are replaced by halogen atoms, wherein the cyclic halogen carbide compound is the compound represented by formula (4):

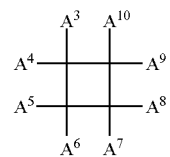

(4)

wherein $A^3$, $A^4$, $A^5$, $A^6$, $A^7$, $A^8$, $A^9$, and $A^{10}$ are the same or different and each is a fluorine atom or a perfluoroalkyl group.

8. A method for producing a halogenated butyne compound represented by formula (3A):

$$CX^1X^2X^3C\equiv CCX^5X^6X^7 \quad (3A)$$

wherein $X^1$, $X^2$, $X^3$, $X^5$, $X^6$, and $X^7$ are the same or different and each is a halogen atom, the method comprising:

(IA) producing the composition containing the halogenated butene compound represented by formula (2A) by the production method according to claim 1;

(IIA) after step (IA), removing hydrogen fluoride; and (IIIA) after step (IIA), subjecting the obtained composition to a dehydrohalogenation reaction in a gas phase to produce the halogenated butyne compound represented by formula (3A):

$$CX^1X^2X^3C\equiv CCX^5X^6X^7 \quad (3A)$$

wherein $X^1$, $X^2$, $X^3$, $X^5$, $X^6$, and $X^7$ are as defined above, wherein the dehydrohalogenation reaction is performed in the presence of at least one catalyst selected from the group consisting of an activated carbon catalyst, a chromium oxide catalyst, and a silica alumina catalyst.

* * * * *